(12) United States Patent
Matsumoto et al.

(10) Patent No.: US 8,811,721 B2
(45) Date of Patent: Aug. 19, 2014

(54) THREE-DIMENSIONAL ULTRASONIC INSPECTION APPARATUS

(75) Inventors: Shin Matsumoto, Saitama (JP);
Takahiro Ikeda, Yokosuka (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 274 days.

(21) Appl. No.: 13/513,685

(22) PCT Filed: Nov. 29, 2010

(86) PCT No.: PCT/JP2010/071223
§ 371 (c)(1),
(2), (4) Date: Jun. 4, 2012

(87) PCT Pub. No.: WO2011/068084
PCT Pub. Date: Jun. 9, 2011

(65) Prior Publication Data
US 2012/0243771 A1 Sep. 27, 2012

(30) Foreign Application Priority Data
Dec. 4, 2009 (JP) .................... 2009-276868

(51) Int. Cl.
*G06K 9/00* (2006.01)
*A61K 49/00* (2006.01)
*G01N 29/06* (2006.01)

(52) U.S. Cl.
CPC ...... *G01N 29/0672* (2013.01); *G01N 2291/106* (2013.01); *G01N 2291/267* (2013.01)
USPC .............................. 382/154; 382/141; 424/9.1

(58) Field of Classification Search
CPC ....................................... G01N 29/0654–29/14
USPC .......... 382/141–152, 154, 285; 715/757, 852; 424/9.1, 9.5; 128/915, 916
See application file for complete search history.

(56) References Cited

U.S. PATENT DOCUMENTS

2007/0130733 A1* 6/2007 Kasai ...................... 24/585.12
2009/0199642 A1* 8/2009 Fukutomi et al. ............. 73/598

FOREIGN PATENT DOCUMENTS

| JP | 63 149559 | 6/1988 |
| JP | 4 265854 | 9/1992 |
| JP | 5 126803 | 5/1993 |
| JP | 11 326287 | 11/1999 |

OTHER PUBLICATIONS

Matsumoto, S. et al., "Three-Dimensional Synthetic Aperture Focusing Technique (3D-SAFT) and Applications", Journal of Society of Automotive Engineers of Japan, vol. 62, No. 7, pp. 84-87, (with English Abstract). (2008).
International Search Report issued on Dec. 21, 2010 in PCT/JP10/071223 filed on Nov. 29, 2010.

* cited by examiner

*Primary Examiner* — Brian Le
(74) *Attorney, Agent, or Firm* — Oblon, Spivak, McClelland, Maier & Neustadt, L.L.P.

(57) ABSTRACT

A three-dimensional ultrasonic inspection apparatus 10 can make increased inspection accuracy in comparison to the conventional apparatus and includes: an ultrasonic transducer 11 disposed m×n piezoelectric vibrators in a matrix; a signal processing unit 17 to receive, detect an echo, and generate a three-dimensional image data by processing an electric signal of the echo detected; a peak detecting element 51, 52 to detect a first peak and a second peak of an intensity distribution of the three-dimensional image data in a depth (z) direction; a joint portion image creation unit 36 to create a three-dimensional image of the joined area 15 by mapping z direction distance of the first peak and the second peak to x-y plane; a determination unit 37 to determine whether the joined area 15 is sound by two-step determination; and a display unit 38 to display the three-dimensional image and the determination result, of the joined area 15.

8 Claims, 8 Drawing Sheets x-y PLANE

A-A' CROSS SECTION

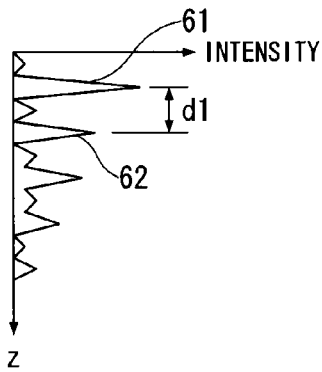 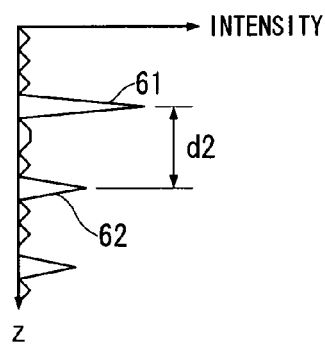 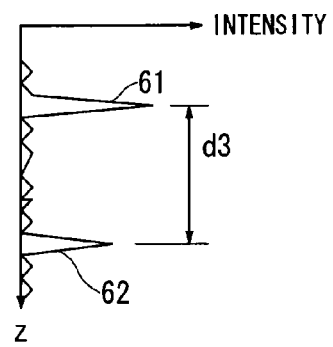
FIG. 6A  FIG. 6B  FIG. 6C
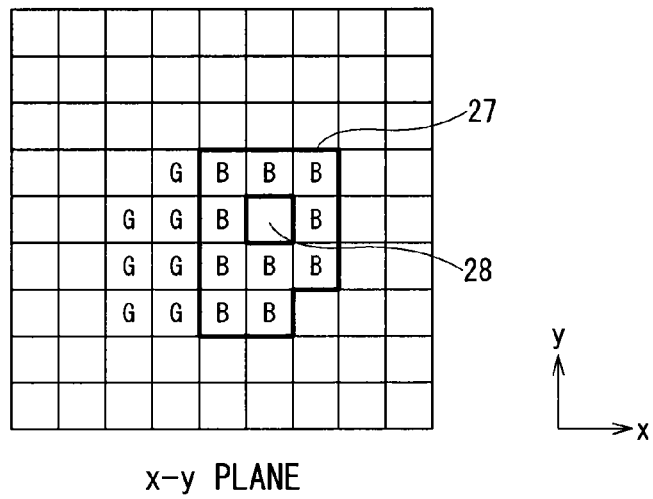
x-y PLANE
FIG. 7

THREE-DIMENSIONAL ULTRASONIC INSPECTION APPARATUS

TECHNICAL FIELD

The present invention relates to a three-dimensional ultrasonic inspection apparatus which performs non-destructive inspection of an inner structure, the state of joined area, and the state of a defect of an object to be inspected, using ultrasonic waves, and more specifically, relates to a three-dimensional ultrasonic inspection apparatus including a sensing device for the ultrasonic inspection, used for an ultrasonic imaging apparatus that three-dimensionally visualizes the state of a welded portion and the state of a weld defect of the object to be inspected.

BACKGROUND ART

An example of technologies that perform non-destructive inspection of the state of a welded portion and the state of a weld defect of a joined area between plate-like structures, an object to be inspected, is an ultrasonic test technology. In an ultrasonic inspection apparatus which adopts the ultrasonic test technology, the ultrasonic waves are irradiated to the welded area of the object to be inspected, and then are reflected from the welded area of the object to be inspected as echoes of the ultrasonic wave. After the reflected echoes of the ultrasonic wave are performed an imaging process, the ultrasonic inspection apparatus displays the reflected echoes performed the imaging process as an ultrasonic wave image, on the display device. The non-destructive inspection a state of the welded area or the weld defect is performed and thereby the user visually determines whether a state of the welded area or the weld defect is sound or not based on the ultrasonic wave image of the welded area.

Specifically, as described in Japanese Unexamined Patent Application Publication No. 11-326287 (Patent Document 1), when a plate-like structure is the object to be inspected, and two plate-like structures are superposed and joined together by means of spot welding, by inspecting the states of the welded portion between the two plate-like structures and a weld defect using the ultrasonic inspection apparatus, in a non-destructive manner, it is possible to inspect whether a molten-solidified portion exists in the welded portion or not, and the presence or absence of the weld defect such as a blowhole, and the state of the weld defect.

Further, as the inspection accuracy of the three-dimensional ultrasonic inspection apparatus constantly improves (increases), the three-dimensional ultrasonic inspection apparatus becomes possible to accurately and quantitatively determinate the state such as the layer structure, the weld defect in the object to be inspected, the presence or absence of the void or the separation, or the likes, of the welded area with respect to the object to be inspected. For example, the three-dimensional ultrasonic inspection apparatus disclosed in Japanese Published Unexamined Patent Application (Patent Laid-Open) No. 2005-315582 (Patent Document 2) inspects the positional relationship of the welded portion with respect to the object to be inspected, correctly, accurately and quantitatively in three dimensions.

PRIOR ART DOCUMENTS

Patent Documents

Patent Document 1 is Japanese Patent Laid-Open No. 11-326287 (JP-A-11-326287); and
Patent Document 2 is Japanese Patent Laid-Open No. 2005-315582 (JP-A-2005-315582).

However, in case of the known three-dimensional ultrasonic inspection apparatus as described in the Patent Document 2, the state of the joined area displayed in the three-dimensional image of the joined area (the joined area image) is not always displayed in a state where the user can easily determine whether the state of the joined area is sound or not. Further, each transparent (see-through) image such as the transparent images of the intermediate portion, the bottom portion or the likes is sliced at the z coordinate being same distance in z direction from each position (x, y) on the surface of object to be inspected. Thus, for example, if a situation that the probe leans a little occurs due to the shape of the object to be inspected or the likes, the intermediate portion or the bottom portion of the object to be inspected is obliquely sliced. Therefore, in this example case, even if the user views (checks) the joined area image, it is difficult for the user to correctly determine whether the state of the joined area is sound or not. Thus, in the method, for the sake of obtaining the transparent image, adopted in the known three-dimensional ultrasonic inspection apparatus as described above, the accuracy of inspecting the joined area may be decreased.

Further, there may occur a stick weld state, i.e, a state where the joined area is tightly joined each other without melting. In case where the stick weld state (non-molten-contacted state) is occurred in the joined area, under the conventional technology, depending on degree of the stick weld state of the joined area, the expert inspector may distinguish between the joined area which does not have acceptable quality because of being in the stick weld state and the joined area which has acceptable quality. However, in the stick weld state, as the ultrasonic wave goes (propagates) through the joined area without reflecting at the joined area, the known three-dimensional ultrasonic inspection apparatus adopted in the conventional technology can not automatically detect the object to be inspected of which the joined area is in the stick weld state as weld defect.

In consideration of above circumstance, an object of the present invention is to provide a three-dimensional ultrasonic inspection apparatus improving easiness and visibility (obviousness) of determining whether the state of joined area is sound or not in comparison to the known ultrasonic inspection apparatus and further improving the inspection accuracy of the joined area because of being possible to obtain precise inspection result of the joined area.

The above mentioned objects can be achieved according to the present invention by providing, in one aspect, a three-dimensional ultrasonic inspection apparatus comprising:

an ultrasonic transducer in which a plurality of piezoelectric vibrators are disposed in a matrix or an array;

a driving element selecting unit to sequentially select piezoelectric vibrators from the plurality of piezoelectric vibrators disposed in the ultrasonic transducer to produce an ultrasonic wave;

a signal detecting circuit to cause the ultrasonic wave generated by the piezoelectric vibrator selected by the drive element selecting unit to propagate through an acoustic wave propagating medium and enter a joined area of an object to be inspected for receiving a reflected echo from the joined area, and to detect an electric signal corresponding to the reflected echo from the joined area;

a signal processing unit to subject the electric signal detected by the signal detecting circuit to signal processing, and to generate three-dimensional imaging data by causing the electric signal to correspond to a mesh element partitioned in a three-dimensional imaging region set inside the object to be inspected;

a first peak detecting unit to detect a first peak of the intensity distribution of the three-dimensional imaging data in depth direction (z direction), the first peak primarily appearing at a depth position being deeper than a reference depth;

a second peak detecting unit to detect a second peak of the intensity distribution of the three-dimensional imaging data in depth direction, the second peak primarily appearing at a depth position being deeper than the depth position at which the first peak appears;

a joint portion image creation unit to create a three-dimensional image of a joined area by mapping a distance, between the depth position at which the first peak appears and the depth position at which the second peak appears, in depth direction at each position on x-y plane;

an open/small determination unit to determine whether a blowhole in the joined area is absent and a size of molten-solidified portion of the joined area satisfies a determination criteria in accordance with the three-dimensional image of the joined area created by the joint portion image creation unit and the determination criteria which is preset;

a stick weld determination unit to determine whether the joined area determined whether the blowhole in the joined area is absent and the size of molten-solidified portion of the joined area satisfies the determination criteria is tightly joined each other without melting; and a display unit to display at least one of the three-dimensional image and at least one of a result determined by the open/small determination unit and a result determined by the stick weld determination unit.

The three-dimensional ultrasonic inspection apparatus according to the present invention can make increased visibility determining whether the state of joined area is sound or not in comparison to the known three-dimensional ultrasonic inspection apparatus then provide the state of joined area, determined on the basis of the three-dimensional image of the joined area to user. Further, since the three-dimensional ultrasonic inspection apparatus according to the present invention can display the determination result whether the state of joined area is sound or not together with the three-dimensional image of the joined area, the three-dimensional ultrasonic inspection apparatus according to the present invention can provide more accurate inspection result to user. Furthermore, in the three-dimensional ultrasonic inspection apparatus according to the present invention, since an accuracy of the determination result whether the state of joined area is sound or not can be increased in comparison to the known ultrasonic inspection apparatus, an accuracy of the three-dimensional ultrasonic inspection can be also increased.

BRIEF DESCRIPTION OF THE DRAWINGS

FIG. 5 (which includes FIGS. 5A and 5B) are explanatory views schematically illustrating a mapping procedure performed by a joined portion image creation unit included in the embodiment of the three-dimensional ultrasonic inspection apparatus according to the present invention, more specifically.

FIG. 6 (which includes FIGS. 6A, 6B and 6C) are explanatory views illustrating intensity distributions in a depth direction (z direction) with respect to each of the meshes m1, m2 and m3 (illustrated in FIG. 5) on the x-y plane more specifically, FIG. 6A is an explanatory drawing illustrating an intensity distribution in the z direction of mesh m1 on the x-y plane, FIG. 6B is an explanatory drawing illustrating an intensity distribution in the z direction of mesh m2 on the x-y plane, and FIG. 6C is an explanatory drawing illustrating an intensity distribution in the z direction of mesh m3 on the x-y plane;

FIG. 7 is an explanatory view illustrating an example of three-dimensional images at the welded portion (joint portion) created by a joint portion image creation unit included in the embodiment of the three-dimensional ultrasonic inspection apparatus according to the present invention;

FIG. 8 (which includes FIGS. 8A and 8B) are explanatory views illustrating principle of the welded state determination (secondary determination) performed by the stick weld portion determination element of the determination unit the display processing device included in the three-dimensional ultrasonic inspection apparatus according to the present invention, more specifically, FIG. 9 (which includes FIGS. 9A and 9B) are explanatory views illustrating path of multiple reflection utilized in the welded state determination (secondary determination) performed by the stick weld portion determination element of the determination unit the display processing device included in the three-dimensional ultrasonic inspection apparatus according to the present invention, more specifically.

BEST MODE FOR CARRYING OUT THE INVENTION

Hereinafter, embodiments of a three-dimensional ultrasonic inspection apparatus according to the present invention will be described with reference to the accompanying drawings.

Figure 1:
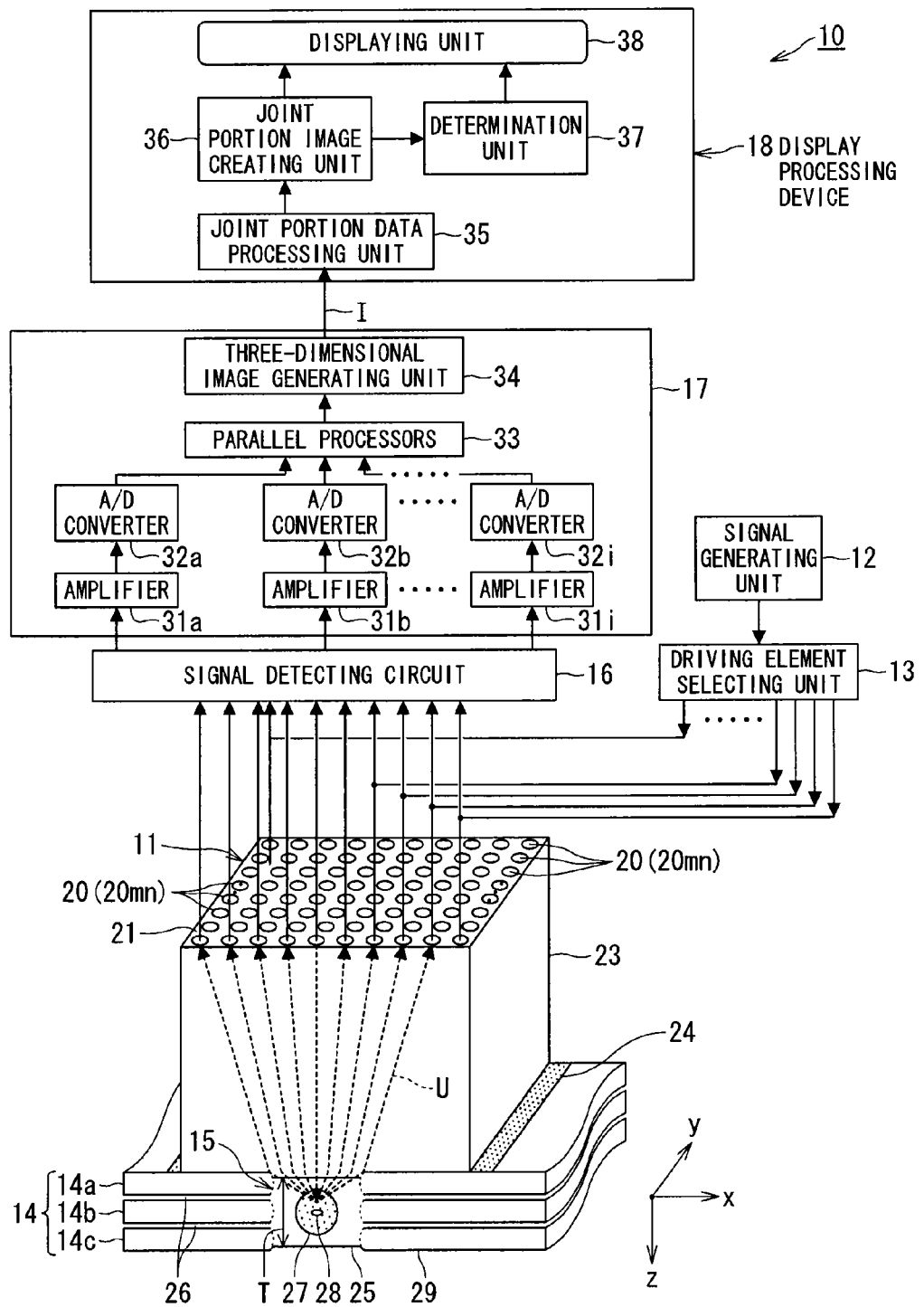
FIG. 1 is a configuration view schematically illustrating an embodiment of the three-dimensional ultrasonic inspection apparatus according to the present invention.

FIG. 1 is a configuration view schematically illustrating a three-dimensional ultrasonic inspection apparatus 10 serving as one embodiment of the three-dimensional ultrasonic inspection apparatus according to the present invention.

The three-dimensional ultrasonic inspection apparatus 10 includes: an ultrasonic transducer 11 as an ultrasonic sensor that causes an ultrasonic vibration to be converted into an electric signal and vice versa, and emits and receives an ultrasonic wave having an required frequency; a signal generating unit 12 for generating a drive signal for driving the ultrasonic transducer 11; a driving element selecting unit 13 for selectively driving a piezoelectric vibrator of the ultrasonic transducer 11 by selecting a drive signal of the signal generating unit 12; a signal detecting circuit 16 including a signal detecting circuit for irradiating an ultrasonic wave produced by the ultrasonic transducer 11 to a welded area 15, which is the joined area of an object (which may includes "inspected-object" hereinafter) to be inspected 14, and then detecting the signal of a reflected echo from the welded area 15 via the ultrasonic transducer 11; a signal processing unit 17 for generating a three-dimensional (3D) ultrasonic image by subjecting an electric signal corresponding to the reflected echo detected by the signal detecting circuit 16 to parallel arithmetic processing; and a display processing device 18 for automatically and accurately determining the states of the internal structure, the joined portion (welded area) 15 and the state of the weld defect 28 by further subjecting the three-dimensional (3D) ultrasonic image processed in the signal processing unit 17 and then displaying the determination result.

The ultrasonic transducer 11 includes a configuration (board) 21 where a large number of piezoelectric vibrators 20 are aligned and arranged in a state of matrix having "m" rows and "n" columns so as to constitute a matrix sensor. A drive signal generated by the signal generating unit 12 is selected by the driving element selecting unit 13 and applied to the each piezoelectric vibrator 20$mn$ of the ultrasonic transducer 11. The piezoelectric vibrators 20$mn$ can be driven individually or in groups, by means of selection of the driving element selecting unit 13, at a required drive timing. Instead of being disposed in a matrix, each piezoelectric vibrator 20 may be arranged in a row or in a cross line so as to constitute an array sensor.

A liquid or solid acoustic wave propagating medium 23 is brought into close contact with the surface for emitting and receiving ultrasonic waves, which is a sensing surface of the ultrasonic transducer 11, specifically, the side of the object to be inspected 14. A couplant 24 for acoustic matching of the ultrasonic waves is provided between the acoustic wave propagating medium 23 and the object to be inspected 14. If a liquid such as water is utilized as the acoustic wave propagating medium 23, the couplant 24 is not required.

Further, when the acoustic wave propagating medium 23 has a shape of a box, the area of an opening of which is formed in accordance with the size of the joined area (portion) 15, which is the inspection region (target region) of the object to be inspected 14, the height of the acoustic wave propagating medium 23 is determined by the oscillation angle (spreading angle) of the ultrasonic wave produced by the piezoelectric vibrators 20.

As the object to be inspected 14, for example, three plate-like structures 14$a$, 14$b$ and 14$c$ joined by means of spot welding, are considered, and a spot welded area of the structures 14$a$, 14$b$ and 14$c$ is subjected to an internal inspection in a non-destructive manner by the three-dimensional ultrasonic inspection apparatus 10 utilizing ultrasonic waves. As the object to be inspected 14, an object having two, four or more pieces of plate-like structures welded by superposing them may be used. The object to be inspected 14 may be a metallic material or a resin material.

When the three plate-like structures 14$a$, 14$b$ and 14$c$ are joined by being superposed and spot welded, a concave portion 25 as a dent portion is formed on the outer surface of the joined area of the plate-like structure 14 by a welding electrode. Thus, the thickness T of the joined area 15 becomes smaller than that of a non-joined area 26 around the joined area 15 by an amount of formation of the concave portion 25.

In FIG. 1, reference numeral 27 denotes molten-solidified portion of the joined area 15, and reference numeral 28 denotes a weld defect such as a blowhole that exists in the joined area 15.

Meanwhile, the signal generating unit 12 for supplying a drive signal to the ultrasonic transducer 11, in order to generate ultrasonic waves by actuating the piezoelectric substance of the piezoelectric vibrators 20, generates a pulsed or continuous drive signal. For the generated drive signal, the piezoelectric vibrators 20$mn$ to be driven by the driving element selecting unit 13 are selected, and the drive signal is supplied to the selected piezoelectric vibrators 20$mn$ at a required timing. Since the driving element selecting unit 13 sequentially selects one or a plurality of the piezoelectric vibrators 20 to be driven at the required timing, when the drive signal from the signal generating unit 12 is supplied to the selected piezoelectric vibrators 20, the piezoelectric vibrators 20 are driven so as to produce an ultrasonic wave U having a required frequency.

The ultrasonic waves sequentially produced by the piezoelectric vibrators 20$mn$ of the ultrasonic transducer 11, pass through the acoustic wave propagating medium 23, enter the object to be inspected 14 via the couplant 24, reach the inspection regions 15 of the object to be inspected 14 (the non-joined area 26, the molten-solidified portion 27, the weld defect portion 28 such as a blowhole, and the bottom portion 29), and are reflected at boundary layers.

The echoes reflected from the boundary layers of the bottom 29, the non-joined area 26, the molten-solidified portion 27, the weld defect portion 28 such as a blowhole of the object to be inspected 14, is input from the object to be inspected 14 to the ultrasonic transducer 11 via the acoustic wave propagating medium 23. In the ultrasonic transducer 11, each reflected echoes is input into piezoelectric vibrators 20 of the ultrasonic transducer 11 used as a matrix sensor, with a different time lag. The reflected echoes input into the piezoelectric vibrators 20 are converted into electric signals and input to the signal detecting circuit 16, where, the electric signals of the reflected echoes are each detected with respect to the corresponding piezoelectric vibrator 20.

In the three-dimensional ultrasonic inspection apparatus 10, when a drive signal is applied to the piezoelectric vibrators 20$mn$ selected by the driving element selecting unit 13, among the piezoelectric vibrators 20 of the ultrasonic transducer 11, the piezoelectric vibrators 20$mn$ operate to produce ultrasonic waves U. The ultrasonic waves U are irradiated to the inspection region, which is the joined area 15 of the object to be inspected 14, via the acoustic wave propagating medium 23 and the couplant 24 if necessary. Portions of the ultrasonic waves U irradiated to the inspection region 15 of the object to be inspected 14 are reflected from a density boundary layer of the inspection region 15 and are reflected as echoes. The reflected echoes are received by the piezoelectric vibrators 20 of the matrix sensor (the ultrasonic transducer 11) with a different time lag via the couplant 24 and the acoustic wave propagating medium 23, transmit to the signal detecting circuit 16 as the electric signals corresponding to the reflected echoes obtained by means of piezoelectric transduction performed by the piezoelectric vibrators 20, and detected.

In the ultrasonic transducer 11, since the piezoelectric vibrators 20mn are sequentially driven at a required timing, by the drive signals which are sequentially supplied from the drive signal selecting unit 13, reflected echoes of the ultrasonic waves produced by the piezoelectric vibrators 20mn are received by the matrix sensor 11 in a two dimensional-manner. When "m" rows (x axis direction) and "n" columns (y axis direction) of the piezoelectric vibrators 20mn (in the example shown in FIG. 1, ten piezoelectric vibrators disposed in x axis direction times eight piezoelectric vibrators disposed in y axis direction totally equals eighty piezoelectric vibrators) are disposed in a matrix, if drive signals are sequentially supplied to the piezoelectric vibrators 20mn by the driving element selecting unit 13, the ultrasonic transducer 11 is configured so that the ultrasonic waves U are sequentially produced by the piezoelectric vibrators 20mn at a timing with which the drive signals are sequentially supplied to the piezoelectric vibrators 20mn, the reflected echoes of the ultrasonic waves sequentially produced by the piezoelectric vibrators 20mn are sequentially received by the matrix sensor 11, and the electric signals corresponding to the reflected echoes, which are the received signals, are transmit to the signal detecting circuit 16 every time the reflected echoes are received.

Consequently, in the signal detecting circuit 16, the reflected echoes of the ultrasonic waves, produced by the individual piezoelectric vibrators 20mn disposed in a matrix by means of operation of the ultrasonic transducer 11, are received by the matrix sensor 11 in a two-dimensional manner. The matrix sensor 11 receives reflected echoes corresponding to the ultrasonic waves produced by the individual piezoelectric vibrators 20mn, the electric signals corresponding to the received reflected echoes are transmitted to the signal detecting circuit 16, and transmitted to the signal processing unit 17 via the signal detecting circuit 16.

The signal detecting circuit 16 has a function of detecting the electric signals corresponding to the reflected echoes produced by the matrix sensor 11. Among the detected signals, a plurality of signals required for inspection are each supplied to one of amplifiers 31a, 31b, . . . , and 31i in the signal processing unit 17.

The amplifiers 31a, 31b, . . . , and 31i have a function of amplifying the supplied electric signals corresponding to the reflected echoes, and to supply the amplified electric signals to A/D converters 32a, 32b, . . . , and 32i, respectively. The A/D converters 32a, 32b, . . . , and 32i have functions of subjecting the supplied electric signals to A/D conversion, and of supplying the converted electric signals to parallel processors 33a, 33b, . . . , and 33i, respectively.

The parallel processors 33 in the signal processing unit 17 have functions of subjecting the digital signals supplied from the A/D converters 32a, 32b, . . . , and 32i, to rapid arithmetic processing in parallel, and of identifying the reflected intensity from mesh elements divided into inspection regions (imaging regions). The identified reflected intensity are unified by a three-dimensional image generating unit 34 into three-dimensional imaging information (data), and transmitted to the display processing device 18. In the display processing device 18, a joint portion data processing unit 35 processes the three-dimensional imaging data transmitted from the three-dimensional image generating unit 34 and transmits processed joint portion data to a joint portion image creation unit 36, the joint portion image creation unit 36 generates the three-dimensional image based on the joint portion data processed by the joint portion data processing unit 35, and a determination unit 37 determines whether the inspection region (target region) is sound (passed) or not (rejected). Meanwhile, in the display processing device 18, a display unit 38 displays the determination result or the three-dimensional ultrasonic image transmitted from the joint portion image creation unit 36 as the ultrasonic test image.

Figure 2:
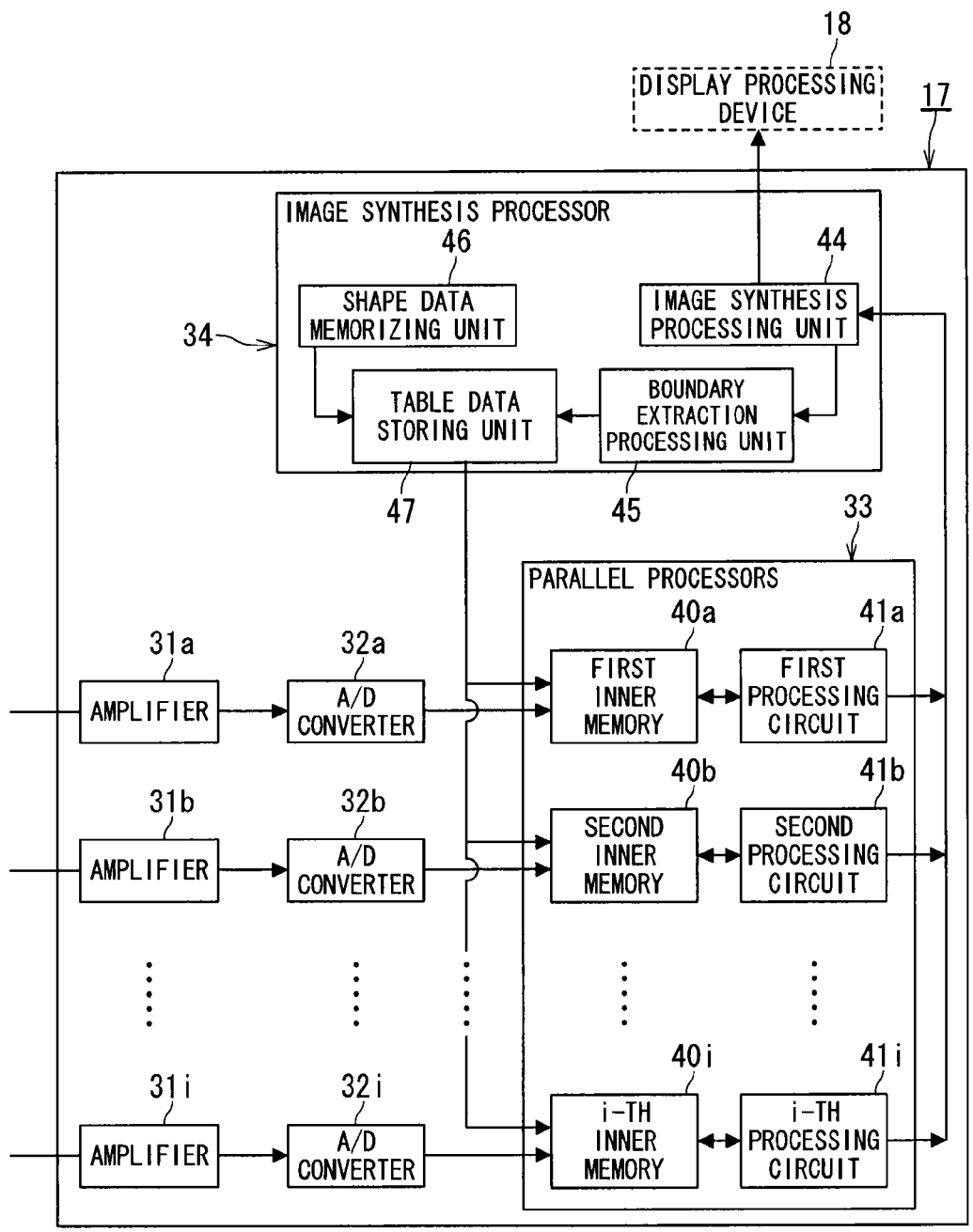
FIG. 2 is a detailed configuration view illustrating a signal processing unit included in the embodiment of the three-dimensional ultrasonic inspection apparatus according to the present invention.

FIG. 2 is a detailed configuration view illustrating a signal processing unit 17 included in the three-dimensional ultrasonic inspection apparatus 10.

The parallel processors 33 and the three-dimensional image generating unit (image synthesis processor) 34 are specifically illustrated in FIG. 2. More specifically, the parallel processors 33 included in the signal processing unit 17 have inner memories 40a, 40b, . . . , and 40i and processing (arithmetic) circuits 41a, 41b, . . . , and 41i, respectively. The three-dimensional image generating unit 34, which is an unified processor, has an image synthesis processing unit 44, a boundary extraction processing unit 45, a shape data memorizing unit 46, and a table data storing unit 47.

The inner memories 40a, 40b, . . . , and 40i have functions of temporarily storing the A/D converted signals supplied from the A/D converters 32a, 32b, . . . , and 32i, and propagation time data obtained by the table data storing unit 47, respectively. The processing circuits 41a, 41b, . . . , and 41i have functions of identifying the reflection intensities from the mesh elements of the imaging region (inspection region) and to cause each mesh element to correspond to a reflection intensity. The reflection intensities corresponding to the mesh elements are supplied to the image synthesis processing unit 44 of the three-dimensional image generating unit (image synthesis processor) 34.

The image synthesis processing unit 44 has a function of generating three-dimensional imaging data by adding the supplied reflection intensities with respect to each mesh element of the inspection region. The generated three-dimensional (3D) imaging data is supplied to the display processing device 18.

Meanwhile, the boundary extraction processing unit 45 has a function of extracting a boundary existing inside the object to be inspected 14 from the result transmitted from the image synthesis processing unit 44. Information regarding the extracted boundary is transmitted to the table data storing unit 47.

The shape data memorizing unit 46 has a function of memorizing the information regarding to the surface shape and the boundary layer structure with respect to the object to be inspected 14, in advance. The memorized information is transmitted to the table data storing unit 47, if required.

The table data storing unit 47 has a function of storing ultrasonic wave propagating times (or equivalent distances may be used) between each of the piezoelectric vibrators 20mn of the matrix sensor 11 in advance by tabling the ultrasonic wave propagating times. A portion or the whole of the stored ultrasonic wave propagating times is transferred to the inner memories 40a, 40b, . . . , and 40i of the parallel processors 33, if required.

Moreover, the ultrasonic wave propagating times stored in the table data storing unit 47 can be reset using the information regarding the extracted boundary in the object to be inspected 14 supplied by the boundary extraction processing unit 45, and the information regarding the surface shape or layer structure with respect to the object to be inspected 14.

In such a manner, the parallel processors 33 and the three-dimensional (3D) image generating unit 34 in the signal processing unit 17 have a function of generating three-dimensional imaging data I for visualizing the state of the joined area 15 by processing the digital signals supplied from the A/D converters 32a, 32b, . . . , and 32i. The three-dimensional imaging data is generated by causing the electric signals corresponding to the reflected echoes, detected by the signal detecting circuit 16, to each correspond to one of the mesh elements of the three-dimensional imaging region set inside the object to be inspected 14 by means of opening-synthesizing processing.

The three-dimensional image generating unit 34 generates three plane (two-dimensional) images by seeing through the three-dimensional imaging data I from three directions, which are a front (X-Y plane) direction viewed from the ultrasonic transducer 11 and two directions (Y-Z plane) and (Z-X plane) perpendicular to the front direction and each other, and projecting the largest data value of the imaging data, superposed in the see-through directions of the three-dimensional imaging data I, in the three directions on a plane. The three-dimensional imaging data I generated by the three-dimensional image generating unit 34 is transmitted to the display processing device 18.

Figure 3:
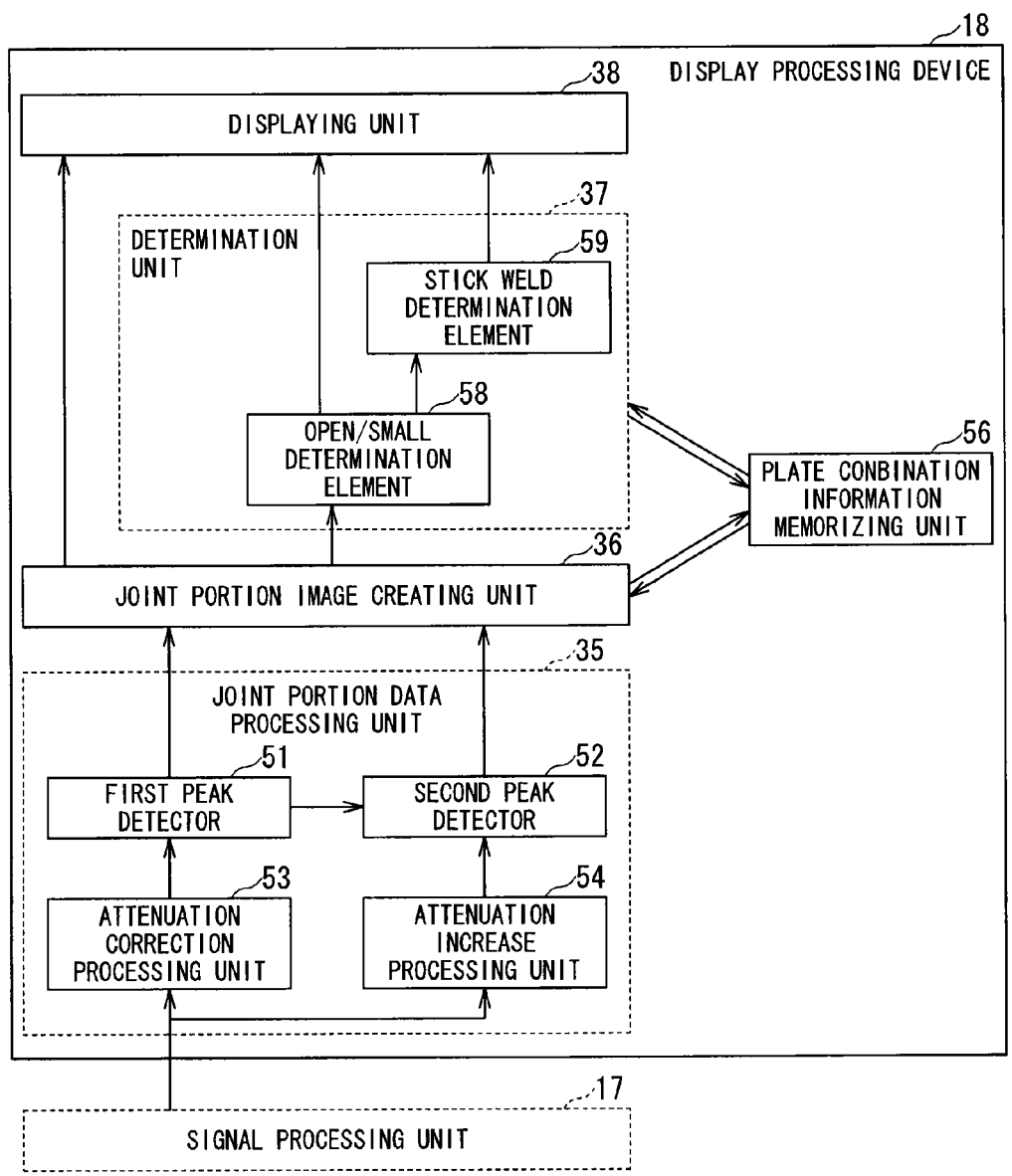
FIG. 3 is a detailed configuration view illustrating a display processing device included in the embodiment of the three-dimensional ultrasonic inspection apparatus according to the present invention.
Figure 4:
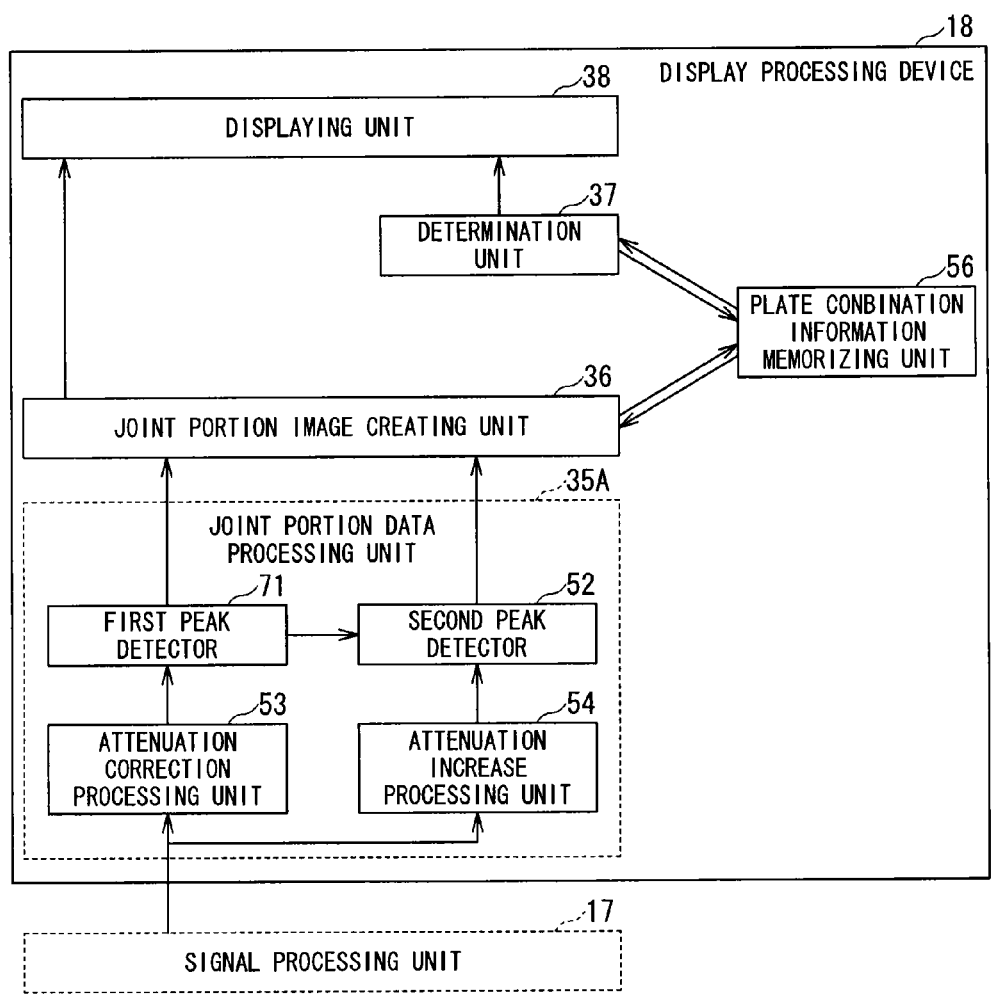
FIG. 4 is a detailed configuration view illustrating another display processing device included in the embodiment of the three-dimensional ultrasonic inspection apparatus according to the present invention.

Each of FIGS. 3 and 4 is detailed configuration view illustrating a display processing device 18 included in the three-dimensional ultrasonic inspection apparatus 10.

For example, the display processing device 18 illustrated in FIG. 3 includes: the joint portion data processing unit 35 which includes a first peak detecting element 51, a second peak detecting element 52, an attenuation correction processing element 53 and an inverse correction processing element (attenuation increase processing element) 54; the joint portion image creation unit 36; and the determination unit 37. Further, if necessary, the display processing device 18 can further include a plate combination information memorizing unit 56 as an information storing unit (which is abbreviated in FIG. 1) for storing information (which at least includes thickness information of each plate (plate-like structure) as components of plate combination), of the object to be inspected (plate combination) 14, which may be used in the joint portion image creation unit 36 and the determination unit 37.

The joint portion data processing unit 35 detects a first peak and a second peak of an intensity distribution, in depth direction (z axis direction) at each point (x, y), which is necessary to create the three-dimensional image of the joined area 15 by utilizing the first peak detecting element 51, the second peak detecting element 52, the attenuation correction processing element 53 and the inverse correction processing element 54.

Herein, the first peak is a peak emerging (appearing) at most nearest (shallowest) position from z=0 in a depth direction of the intensity distribution (illustrated in FIG. 6 mentioned below) of the three-dimensional imaging data I. The second peak is a peak emerging (appearing) at a position where is deeper than the first peak emerging position in the object to be inspected 14 in a depth direction of the intensity distribution of the three-dimensional imaging data I. Further, peaks 61 and 62 illustrated in FIG. 6 mentioned below will be described as the first peak 61 and the second peak 62.

The joint portion image creation unit 36 creates the three-dimensional image of the joined area 15 by utilizing the first peak and the second peak, of an intensity distribution in depth direction (z axis direction) at each point (x, y), respectively detected by the joint portion data processing unit 35.

The determination unit 37 determines whether the state of the joined area 15 is sound or not in accordance with the three-dimensional image of the joined area 15 created by the joint portion image creation unit 36 and welded state determination criteria which have two different stages. As illustrated in FIG. 3, more specifically, the determination unit 37 includes: an open/small determination element 58 to determine whether the state of the joined area 15 is sound or not as a first determination stage; and a stick weld determination element 59 to determine whether the state of the joined area 15 is sound or not as a second determination stage; and thereby determines whether the state of the joined area 15 is sound or not through two different welded state determination stages.

Here, the open/small means that the joined area 15 is open state and/or small state. The open state means that the joined area 15 has the blowhole (void) and therefore is partly open as a space. The small state means that a size of molten-solidified portion of the joined area 15 does not satisfy welded criteria, that is, a size of molten-solidified portion of the joined area 15 is smaller than a minimum size which satisfies the welded criteria. Therefore, in a case where the joined area 15 is at least one of open state and small state, the joined area 15 is determined as "rejection (rejectable quality)". Meanwhile, in a case where the joined area 15 is neither open state nor small state, the joined area 15 is determined as "acceptance (acceptable quality)".

The joint portion data processing unit 35, the joint portion image creation unit 36, the determination unit 37 and the plate combination information memorizing unit 56 in the display processing device 18 will be described.

The first peak detecting element 51 of the joint portion data processing unit 35 is a configuration element to detect the first peak of the intensity distribution of the three-dimensional imaging data I in a depth direction. The first peak detecting element 51 includes a function (first peak detecting range setting function) of receiving a searching range for detecting the first peak and holding (setting) the searching range, a function (first peak detecting function) of detecting a peak of maximum intensity in the searching range as the first peak and a function (surface position measuring function) of measuring a position of the surface (which is a face on the side of the couplant 24) of the object to be inspected 14.

In accordance with a search range of the first peak preliminarily set by the user, the first peak detecting element 51 detects each peak of maximum intensity at each point (x, y) corresponding to each mesh in the search range of the first peak. Subsequently, the first peak detecting element 51 measures each position (z coordinate) of the first peak detected at each point (x, y), and then measures the surface (which is located at the couplant side) by utilizing each position (z coordinate) of the first peak detected at each point (x, y) in the search range of the first peak. In this time, the first peak detecting element 51 also measures the indentation depth (t illustrated in FIG. 5).

The second peak detecting element 52 is a configuration element to detect the second peak of the intensity distribution of the three-dimensional imaging data I in a depth direction and substantially includes equivalent functions of the first peak detecting element 51. That is, the second peak detecting element 52 includes a second peak detecting range setting function of receiving a searching range for detecting the second peak and holding (setting) the searching range, a second peak detecting function of detecting a peak of maximum intensity in the searching range as the second peak, and a bottom position measuring function of measuring a position of the bottom 29 of the objection to be inspected 14.

In accordance with a search range of the first peak preliminarily set by the user, the second peak detecting element 52 detects each peak of maximum intensity at each (x, y) corresponding to each mesh in the search range of the second peak. Subsequently, the second peak detecting element 52 measures each position (z coordinate) of the second peak detected at each position (x, y), and then measures the bottom surface (which is located at a bottom side) 29 by utilizing each position (z coordinate) of the second peak detected at each position (x, y) in the search range of the second peak. In this time, the second peak detecting element 52 also measures the indentation depth (t illustrated in FIG. 5).

The search range of the second peak is set so that a z coordinate at which the second peak exists is always larger (deeper) than the z coordinate at which the first peak exists. For example, if the z coordinate at which the first peak exists is z1 (z=z1), the z coordinate (z=z1+α) obtained by adding predetermined depth (for example, α) to z1 serving as the position (z coordinate) at which the first peak exists is set as a starting position in a case where the second peak detecting element 52 searches the second peak.

For the sake of preventing the attenuation correction processing element 53 from faultily detecting an echo (bottom echo) of the acoustic wave propagating medium 23 as the first peak, the bottom echo reflected from the bottom 29, in a case where the acoustic wave propagating medium 23 is not tightly attached to the plate-like structure 14*a*, the attenuation correction processing element 53 performs a correction processing (which will be referred to as "attenuation correction processing", hereinafter) so as to increase an intensity of the reflection echo in depth direction (z direction) of the three-dimensional image data of the object to be inspected 14 as a depth increases. In more detail, by utilizing following expression 1, the attenuation correction processing element 53 calculates the intensity distribution F(v) in z direction after attenuation correction processing.

$$F(v)=v/rz \quad \text{[Expression 1]}$$

v: reflection intensity in depth z
r: correction coefficient
z: depth

The attenuation correction processing element 53 includes a storage region for storing information and stores necessary information for performing the attenuation correction processing such as information of the expression 1 utilized for the attenuation correction processing, each parameter information, information of a setting value (0<r<1) of the correction coefficient r or the likes in the storage region. The attenuation correction processing element 53 obtains the intensity v at depth z obtained on the basis of the three-dimensional imaging data I, the depth z, the correction coefficient r and mathematical expression (=v/rz) for calculating the expression 1 and then calculates F(v) described in the expression 1.

The attenuation correction processing is a correction processing for preventing from faultily detecting the bottom echo of the acoustic wave propagating medium 23 as the first peak in a case where the acoustic wave propagating medium 23 is not tightly attached to the plate-like structure 14*a*. The attenuation correction processing is not necessarily performed in a case where the acoustic wave propagating medium 23 is tightly attached to the plate-like structure 14*a* and thereby the attenuation correction processing element 53 correctly detects the first peak without the false detection of the first peak. That is, the attenuation correction processing is an optional processing (auxiliary processing) for correctly detecting the first peak and performed as necessary.

As the attenuation correction processing is the optional processing and need not necessarily performed, the attenuation correction processing element 53 is configured to be capable of switching to whether the attenuation correction processing is performed or not in accordance with the user's selecting operation. When the user's selecting operation allows the attenuation correction processing element 53 to perform the attenuation correction processing, the attenuation correction processing element 53 performs the attenuation correction processing. Namely, as the attenuation correction processing of the attenuation correction processing element 53 is a processing for obtaining the intensity (which the attenuation correction processing is performed) F(v) which is stronger than the original intensity (which the attenuation correction processing is not performed) v by increasing the original intensity v, the correction coefficient r becomes a positive number (0<r<1) which is smaller than one.

For the sake of preventing the inverse correction processing element 54 from faultily detecting a high-order peak, other than the second peak, such as third peak, fourth peak or the likes, the high-order peak being repeated echo of the second peak, the inverse correction processing element 54 performs a processing (which will be referred to as "inverse correction processing", hereinafter) so as to be forced to attenuate the intensity of the reflection echo in depth direction (z direction) of the three-dimensional image data of the object to be inspected 14 as a depth increases.

The false detection of the second peak occurs in a case where the intensity of the third peak, fourth peak or the likes, emerging at depth position deeper than the depth position at which the second peak emerges, is stronger than the intensity of the second peak. For example, if the first peak emerges at shallow position, a scope (range) searching the second peak is also set in shallow position. In theory, as the high-order peak other than the second peak such as the third peak, the fourth peak or the likes is the repeated echo of the second peak, the intensity of the third peak or the fourth peak should not be stronger than the intensity of the second peak. However, in actuality, the intensity of the third peak or the fourth peak occasionally becomes stronger than the intensity of the second peak because of a contact state between the ultrasonic transducer 11 and the object to be inspected 14, a surface state of the object to be inspected 14 and so on. In case where the false detection of the second peak as described above may be occurred, the inverse correction processing element 54 is useful.

The difference between the attenuation correction processing element 53 and the inverse correction processing element 54 is each setting value of the correction coefficient r stored in each element 53, 54. Specifically, the correction coefficient r stored in the attenuation correction processing element 53 is set a positive number (r>1) which is larger than one and the correction coefficient r stored in the inverse correction processing element 54 is set a positive number (0<r<1) which is smaller than one. However, the basic construction of the attenuation correction processing element 53 and the inverse correction processing element 54 is not substantially different. The inverse correction processing performed by the inverse correction processing element 54 is an optional processing (auxiliary processing), for correctly detecting the second peak being similar to the attenuation correction processing. That is, the inverse correction processing element 54 performs the inverse correction processing if necessary.

Further, although the joint portion data processing unit 35A illustrated in FIG. 4 has similarities in the joint portion data processing unit 35 illustrated in FIG. 3 in point of detecting the first peak, the joint portion data processing unit 35A differs from the joint portion data processing unit 35 in that the joint portion data processing unit 35A includes a first peak detecting element 71 adopting detection method being different from those of the first peak detecting element 51 instead of the first peak detecting element 51. As the joint portion data processing unit 35A is not substantially different from the joint portion data processing unit 35 in the other points, the same reference numerals or characters in FIG. 4 are assigned to the same or similar components as those in FIG. 3, and the description thereof is omitted.

The first peak detecting element 71, with respect to the first peak detecting element 51, further has a function (first peak false detection prevention function) of preventing from false detection of the first peak. As the first peak detecting element 71 has the first peak false detection prevention function, the first peak detecting element 71 can prevent from faultily detecting the bottom echo of the acoustic wave propagating medium 23 as the first peak in a case where the acoustic wave propagating medium 23 is not tightly attached to the plate-like structure 14a.

In case where the bottom echo of the acoustic wave propagating medium 23 is not tightly attached to the plate-like structure 14a, phase reversal of the reflection echo occurs. Although a phase of the bottom echo of the acoustic wave propagating medium 23 does not reverse, a phase of the echo reflected at the plate-like structure 14a reverses. Thus, the first peak false detection prevention function of the first peak detecting element 71 can be realized by means of using the phase reversal. In other words, since the first peak detecting element 71 can determine whether the bottom echo of the acoustic wave propagating medium 23 or the echo reflected at the plate-like structure 14a by detecting whether the phase reversal occurs or not, the first peak detecting element 71 can prevent from faultily detecting the bottom echo of the acoustic wave propagating medium 23 as the first peak.

The joint portion data processing unit 35, configured in such a manner, detects the first and second peaks of the intensity distribution in depth direction (z axis direction) at each position (x, y) and measures each position of the surface and the bottom 29 of the object to be inspected 14 based on each z coordinate at each position (x, y) of the first peak and the second peak detected by the joint portion data processing unit 35.

The joint portion image creation unit 36 included in the display processing device 18 will be described with reference to FIGS. 5, 6 and 7.

Figure 5A:
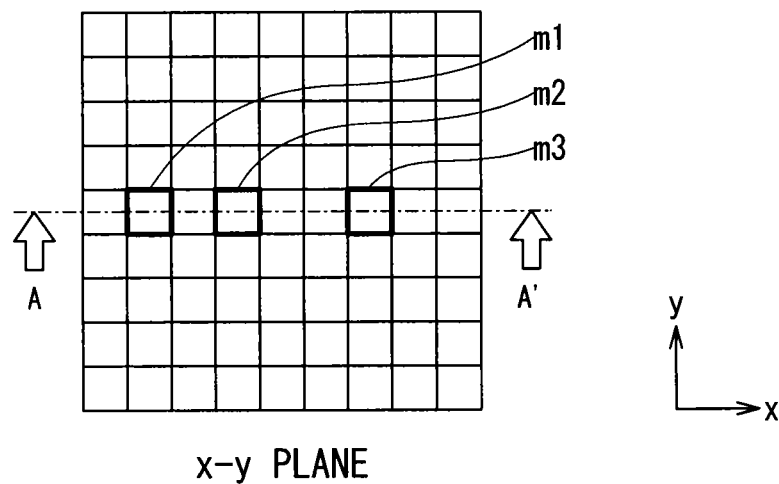
FIG. 5A is an explanatory drawing illustrating a relation between a x-y plane subjected to the mapping procedure and mesh and FIG. 5B is an explanatory drawing illustrating a cross-section (z-x plane) of an object to be inspected along a line A-A' illustrated in FIG. 5A.
Figure 5B:
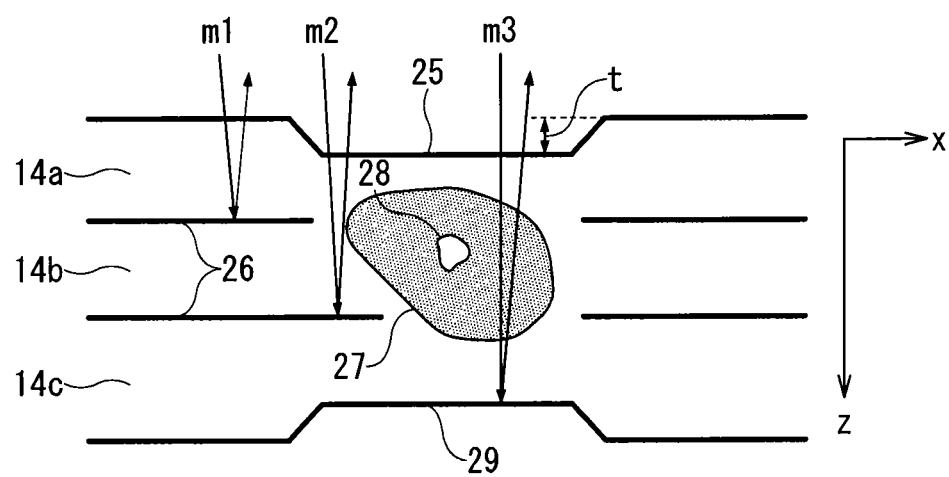

FIG. 5 (which includes FIGS. 5A and 5B) is an explanatory view schematically illustrating a mapping procedure performed by the joined portion image creation unit 36. In more detail, FIG. 5A is an explanatory view schematically illustrating a relation between a x-y plane subjected to the mapping procedure and the meshes of the x-y plane. FIG. 5B is an explanatory view schematically illustrating the mapping procedure performed by a joined portion image creation unit 36. Herein, reference "t" illustrated in FIG. 5B denotes the indentation depth.

FIG. 6 (FIGS. 6A, 6B and 6C) are explanatory views illustrating intensity distributions in a depth direction (z direction) with respect to each of the meshes m1, m2 and m3 (illustrated in FIG. 5) on the x-y plane. Herein, FIGS. 6A, 6B and 6C are respectively corresponding to three meshes m1, m2 and m3 illustrated in FIG. 5.

FIG. 7 is an explanatory view illustrating an example of three-dimensional images at the welded portion (joint portion) 15 created by a joint portion image creation unit 36. Herein, the blank mesh, the mesh denoted by "G" and the mesh denoted by "B" illustrated in FIG. 7 respectively denotes red mesh, green mesh and blue mesh.

With respect to each position (x, y) detected by the joint portion data processing unit 35, the joint portion image creation unit 36 calculates each depth position, at which the ultrasonic reflection occurs, with respect to each mesh on the x-y plane based on the first and second peaks 61 and 62 of the intensity distributions in a depth direction (z direction).

For example, as illustrated in FIG. 5B, regarding each mesh m1, m2 and m3 illustrated in FIG. 5A, it assumes that a depth position, at which the ultrasonic wave reflection occurs is the non-joined area 26 located at area between a first plate-like structure 14a and a second plate-like structure 14b, of the mesh m1, a depth position, at which the ultrasonic wave reflection occurs is the non-joined area 26 located at area between the second plate-like structure 14b and a third plate-like structure 14c, of the mesh m2, and a depth position, at which the ultrasonic wave reflection occurs is the bottom surface 29, of the mesh m3.

For the sake of measuring each depth position at which the ultrasonic wave reflection occurs, with respect to each mesh, the joint portion image creation unit 36 calculates (measures) each distance d between the first and second peaks 61 and 62, of the intensity distributions in a depth direction (z direction), of each position (x, y) as illustrated in FIG. 6. In example of the meshes m1, m2 and m3 illustrated in FIG. 5, each depth of the depth positions, at which the ultrasonic wave reflection occurs, of each mesh m1, m2 and m3 is calculated (measured) as each depth d1, d2 and d3 (d1<d2<d3).

After each depth position, with respect to each mesh, at which the ultrasonic wave reflection occurs is calculated, the joint portion image creation unit 36 obtains the three-dimensional image of the joined area 15 (the joined area image) by performing the mapping procedure with respect to each mesh. The joint portion image creation unit 36 determines that a color, of each mesh, corresponding to the calculated depth based on a relation between predetermined depth range and the color displayed on the display unit 38. Subsequently, the joint portion image creation unit 36 plots the determination result (determined color) on each mesh.

For example, as illustrated in FIG. 7, it is assumed that the color of the mesh is set as red (illustrated as the blank mesh in FIG. 7) in a case where the proportion the calculated depth of whole thickness of the object to be inspected 14 is within a range from zero to one third (0-⅓), the color of the mesh is set as green (illustrated as the reference "G" in FIG. 7) in a case where the proportion the calculated depth of whole thickness of the object to be inspected 14 is within a one third to two-thirds (⅓-⅔), and the color of the mesh is set as blue (illustrated as the reference "B" in FIG. 7) in a case where the proportion the calculated depth of whole thickness of the object to be inspected 14 is within a range from two-thirds to one (⅔-1). In this case, after the color corresponding to the calculated depth is determined with respect to each of the meshes, the color of each mesh should be displayed. Incidentally, while each depth range is set without considering some errors in this example, each depth range may be set in consideration of some errors.

In such a manner, when the color of each position (x, y) is determined, the joint portion image creation unit 36 can obtain the joined area image as illustrated in FIG. 7 by coloring each mesh in the color determined with respect to each of the meshes. In the example case illustrated in FIG. 7, as the blue mesh shows a region where the plate-like structures 14a, 14b and 14c is joined by welding, the green mesh shows a region where the plate-like structures 14a and 14b is joined by welding, and the red mesh shows a region where the plate-like structures 14a, 14b and 14c is not joined by welding at all or the weld defect portion 28 emerges, the user can easily determine the state of the joined area 15 even if the user has only to view (check) the three-dimensional image of the joined area 15 (the joined area image).

In this embodiment, while the object to be inspected 14 is configured by three plate-like structures 14a, 14b and 14c, the object to be inspected 14 may be two, four or more plate-like structures. Further, even if the number of the plate-like structures is increased, by setting the number of a color utilizing for mapping procedure being equal or lager than the number of the plate-like structures, the joint portion image creation unit 36 can create the joined area image enabling the user to determine the number of the plate-like structures are joined by welding as same example explained above.

Moreover, the joint portion image creation unit 36 has a function of detecting and measuring the size and the position of the joined area 15 and the size and the position of the weld defect portion 28. The joint portion image creation unit 36 can measure the size and the position of the joined area 15 in the object to be inspected 14 and the size and the position of the weld defect portion 28 in the object to be inspected 14.

In the joint portion image (x-y Plane) illustrated FIG. 7, an outer side boundary (which is heavy line illustrated in FIG. 7) between the blue mesh and other mesh (the green mesh or the red mesh) is displayed as the profile shape of the joined area 15. In case where the weld defect portion 28 such as a blowhole exists in the joined area 15, closed red regions (continuum region, determined as same depth range being different from range of depth corresponding to blue continuum region by the joint portion image creation unit 36, corresponding to one blank mesh enclosed in eight blue meshes in example illustrated in FIG. 7), existed in continuum blue region (continuum region determined as same depth range by the joint portion image creation unit 36) are separately displayed as the weld defect portion 28 such as a blowhole. That is, the profile shape of the weld defect portion 28 is displayed as the border line (boundary) between continuum blue region and continuum red region.

In case where the weld defect portion 28 does not exist in the joined area 15, the red mesh does not emerge in the blue meshes successively existed in the joint portion image. Further, in some case, for example, such as the case where the weld defect portion 28 exists near the non-joined area 26 located at area between the second plate-like structure 14b and a third plate-like structure 14c or the likes, the weld defect portion 28 may be shown as closed green region in blue continuum region or mixed-region existing the red region and the green region.

By utilizing the three-dimensional image, of the joined area 15 (the joined area image), obtained in such a manner, the joint portion image creation unit 36 can determine a size of the joined area 15 and a center position of the joined area 15 on the basis of a profile shape of the joined area 15 and a profile shape of the weld defect portion 28. Further, there is a case where, in the joined area image, continuum region determined as same depth range in x-y plane, such as the blank mesh illustrated in FIG. 7 is exist in another continuum region determined as same depth range in x-y plane, such as the blue mesh illustrated in FIG. 7. In above case, the joint portion image creation unit 36 considers the continuum region enclosed in the another continuum region as the weld defect portion 28 and thereby can determine a size of the weld defect portion 28 and a center position of the weld defect portion 28 based on the profile shape of the weld defect portion 28.

It should be noted that it is not limited to the above described example, such as the mapping method, the color selection of mapping, the number of display level (the number of devising the depth of the object to be inspected 14) or the likes, the above described example adopted when the joint portion image creation unit 36 created the three-dimensional image, of the joined area 15 (the joined area image). The above described example can be arbitrarily selected from any kinds of options in design.

For the purpose of improving the image created by the joint portion image creation unit 36 and an accuracy of determination determined by the determination unit 37, the plate combination information memorizing unit 56 includes a storage region for storing the information, of each thickness of each plate-like structure as the object (plate combination) to be inspected 14, the information which the joint portion image creation unit 36 and the determination unit 37 utilize as needed.

For example, when each plate thickness of the objection (plate combination) to be inspected 14 is nearly equal, even in consideration of the measurement error, there is little occurrence of a false detection, such that the depth position shown in green is determined as the depth position shown in blue, the depth position shown in red is determined as the depth position shown in green or the likes. However, when each thickness of the objection to be inspected 14 configured by the plate-like structures is different, the joint portion image creation unit 36 may faultily detect the depth position in a setting as exemplified above. Thus, in such a manner, the plate combination information stored in the plate combination information memorizing unit 56 is utilized as clue upon determining each color for the mapping procedure with respect to each mesh on the x-y plane. In more detail, at first, the joint portion image creation unit 36 determines distance in depth direction (position of depth "d") corresponding to depth position, obtained by referring to the plate combination information stored in the plate combination information memorizing unit 56, the depth position at which three plate-like structures 14a, 14b and 14c are respectively joined. Subsequently, the joint portion image creation unit 36 determines each color for the mapping procedure with respect to each mesh on the x-y plane in accordance with determined depth position.

For example, if each thickness of the plate-like structures 14a, 14b and 14c, illustrated in FIG. 5, as the object (plate combination) to be inspected 14 is respectively "ta", "tb" and "tc" (ta≠tb≠tc>0), an allowable error is "e", a depth calculated at position (x, y) is "d", the joint portion image creation unit 36 can determine a color (which will be referred to as "mesh color", hereinafter) which the joint portion image creation unit 36 subjects the mesh existed at position (x, y) to perform the mapping procedure in accordance with following expression (condition expression) 2. In the expression 2, in a case where the condition expression which is satisfied is: the condition expression (1); the condition expression (2); and the condition expression (3), for example, the mesh color is respectively determined as red, green and blue.

[Expression 2]

$$d < ta + e \tag{1}$$

$$ta + tb - e < d < ta + tb + e \tag{2}$$

$$ta + tb + tc - e < d < ta + tb + tc + e \tag{3}$$

Herein, reference characters "ta", "tb" and "tc" respectively denote the thickness of the plate-like structures 14a, 14b and 14c, reference character "e" denotes allowable error and reference character "d" denotes depth calculated at (x, y). The allowable error e of the upper limit value of the depth d and the allowable error e of the lower limit value of the depth d may be differently set.

The joint portion image creation unit 36 transmits a measurement result of the size and position of the joined area 15 of the object to be inspected 14 and the size and position of the weld defect portion 28, the measurement result measured on the basis of the three-dimensional image of the joined area 15 to the determination unit 37 and the display unit 38.

The determination unit 37 determines whether the joined area 15 is sound or not in accordance with the joined area image input from the joint portion image creation unit 36 and, the information of determination criteria, mathematical expressions and parameters, utilized in the determination criteria, the information stored in the determination unit 37 through two different welded state determination stages. More specifically, the open/small determination element 58 of the determination unit 37 performs the open/small determination which is the first stage (which will be referred to as "primary determination", hereinafter) of the welded state determination whether the joined area 15 is sound or not. The stick weld determination element 59 of the determination unit 37 performs a stick weld determination which is the second stage (which will be referred to as "secondary determination", hereinafter) of the welded state determination whether the joined area 15 is sound state or the stick weld state.

It is difficult to correctly determine whether the joined area 15 is in the stick weld state or not based only on the joined area image obtained from the joint portion image creation unit 36. That is, in a case where there is not the blowhole (void) in the joined area 15, the size of the joined area 15 satisfied the welded criteria, and the joined area 15 is not molten-solidified, even if the joined area 15 being in the stick weld state included in the object to be inspected 14 is inspected, since it is impossible to distinguish between the stick weld state (which should be determined as "rejection") and a state (which should be determined as "acceptance") where the joined area 15 is correctly welded, the stick weld state of the joined area 15 can not be detected. This is the reason why the determination unit 37 determines whether the joined area 15 is sound or not through the open/small determination as the primary determination and the stick weld determination as the secondary determination. Further, as obvious reflection at the non-joined portion which is in the open state is occurred, a portion being in the open state can be mapped as the green region or the red region. Meanwhile, as the ultrasonic (reflection) echo occurred by reflecting at the joined area 15 being in the stick weld state is much weak, it is difficult to correctly detect a peak of the reflection echo caused by reflecting at the joined area 15 being in the stick weld state as the second peak 62. This is the reason why the stick weld state of the joined area 15 can not be detected.

Accordingly, in view of improvement of accuracy determining whether the joined area 15 is sound or not, it is important that accuracy determining whether the stick weld portion in the joined area 15 is present or absent is improved. Therefore, the determination unit 37 is configured to perform the open/small determination as the primary determination and then the stick weld determination as the secondary determination. In the primary determination, the determination unit 37 excludes the object to be inspected 14 determined as the open state or the small state from the object to be determined whether the joined area 15 is sound or not. In the secondary determination, with respect to the object to be inspected 14 accepted (passed) in the primary determination, the determination unit 37 determines whether the stick weld portion in the joined area 15 is present or absent.

In the open/small determination as the primary determination, the open/small determination element 58 determines whether the joined area 15 is the open/small state or not. The open/small state means that there is the blowhole (void) in the joined area 15 and/or the size of the joined area 15 does not satisfy the welded criteria. In case where there is not the blowhole (void) in the joined area 15 and the size of the joined area 15 satisfied the welded criteria, the open/small determination element 58 determines as "acceptance". In case where the object to be inspected 14 is determined as "acceptance" by the open/small determination element 58, the stick weld determination element 59 performs the stick weld determination as the secondary determination, and thereby determines whether the joined area 15 is sound or not. Meanwhile, in a case where the object to be inspected 14 is determined as "rejection" by the open/small determination element 58, the welded state determination whether the joined area 15 is sound or not is completed.

In the stick weld determination as the secondary determination, the stick weld determination element 59 determines whether the joined area 15 is in the stick weld state or not. That is, the stick weld determination element 59 determines whether the size of region determined as the molten-solidified portion of the joined area 15 by the open/small determination element 58 is larger than a minimum size which satisfies the welded criteria and the plate-like structures are tightly joined each other with out melting or not. Specifically, the stick weld determination element 59 focuses the region determined as the molten-solidified portion of the joined area 15, checks intensity of the reflection echo (more properly, which is present near the bottom of the first plate-like structure 14a) between the first peak 61 and the second peak 62, and thereby determines whether the joined area 15 is in the stick weld state or not.

In comparison between the object (which will be referred to as "normal object", hereinafter) to be inspected 14 which includes the joined area 15 not being in the stick weld state (normal state) and the object to be inspected 14 which includes the joined area 15 being in the stick weld state, in a region near the bottom of the first plate-like structure 14a, the intensity of the reflection echo obtained from the object to be inspected 14 which includes the joined area 15 being in the stick weld state is different from the intensity of the reflection echo obtained from the object to be inspected 14 being in the normal state. When the intensity of the reflection echo obtained from the object to be inspected 14 which includes the joined area 15 being in the stick weld state is compared to the intensity of the reflection echo obtained from the object to be inspected 14 being in the normal state, the intensity of the reflection echo obtained from the object to be inspected 14 being in the normal state is slightly stronger than the intensity of the reflection echo obtained from the object to be inspected 14 which includes the joined area 15 being in the stick weld state. Therefore, the stick weld determination element 59 determines whether the joined area 15 is in the stick weld state or not based on a difference between the intensity of the reflection echo obtained from the object to be inspected 14 which includes the joined area 15 being in the stick weld state and the intensity of the reflection echo obtained from the object to be inspected 14 being in the normal state.

Further, in view of detecting whether the joined area 15 is in the stick weld state or not, the inventors obtain (find) knowledge (finding) that it is effective for improving accuracy of the secondary determination to using information based on the intensity of the reflection echo, which appears at a depth position between the depth position at which the second peak appears and the depth position at which a third peak following the second peak appears, in other words, the reflection echo obtained from the multiple reflection wave. That is, the inventor's knowledge is that the accuracy of the secondary determination in case of using the information based on the reflection echo obtained from the multiple reflection wave is superior to the accuracy of the secondary determination in case of using information based on the intensity of the reflection echo, which appears at a depth position between the depth position at which the first peak appears and the depth position at which the second peak appears. Thus, the stick weld determination element 59 of the determination unit 37 applied to the display processing device 18 of the three-dimensional ultrasonic inspection apparatus 10 utilizes the intensity of the ultrasonic echo occurred by the multiple reflection and thereby determines whether the joined area 15 is in the stick weld state or not. It is noted that the inventor's knowledge does not prevent from using the intensity of the reflection echo which is present between the first peak 61 and the second peak 62 in the secondary determination performed by the stick weld determination element 59.

The second stage of welded state determination performed by the stick weld determination element 59 will be described with reference to FIGS. 8 and 9, i.e., FIGS. 8A, 8B, 9A and 9B.

Figure 8A:
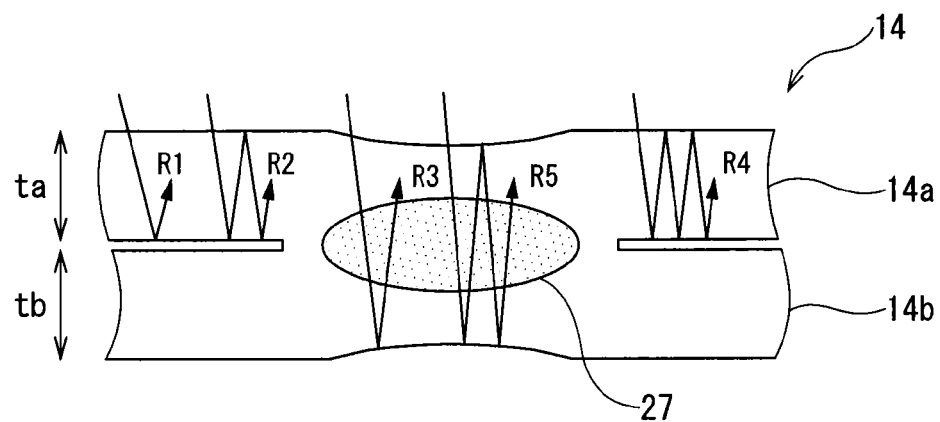
FIG. 8A is a cross-sectional view (of z-x plane) of object to be inspected illustrating an example of real reflection (direct reflection and multiple reflection) occurring in the z-x plane.
Figure 8B:
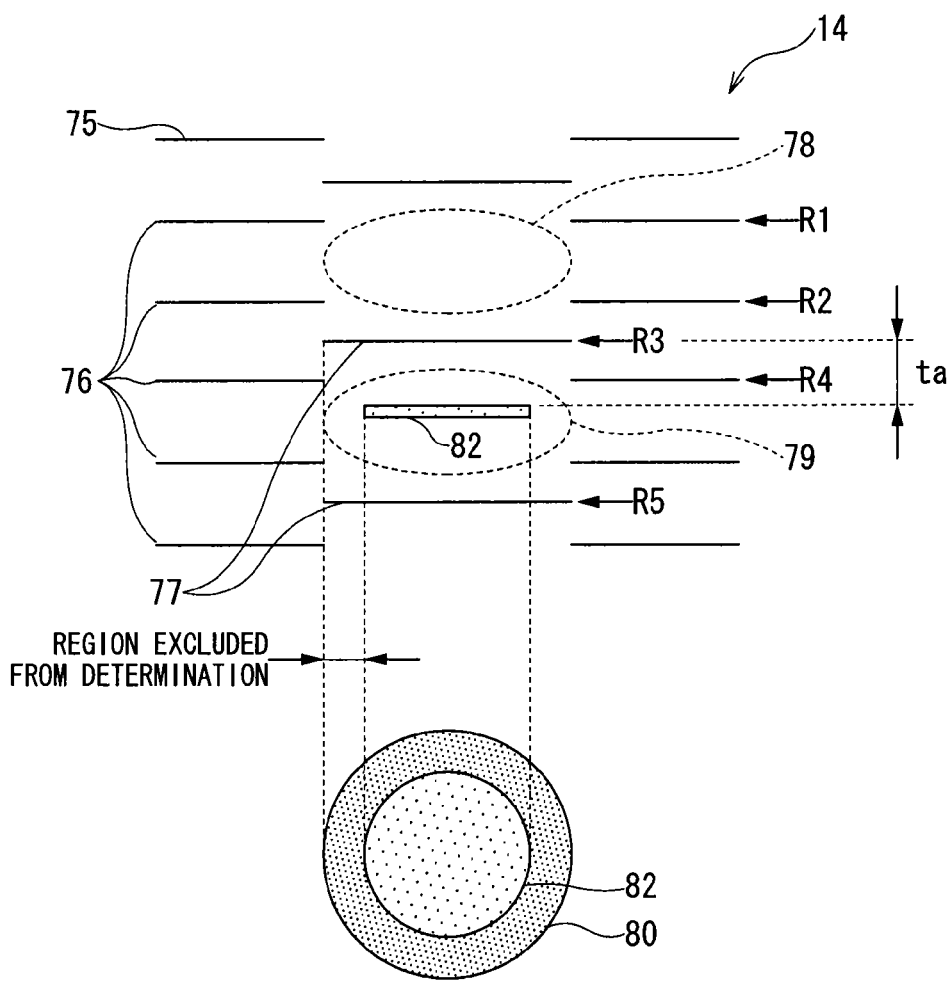
FIG. 8B is an explanatory drawing illustrating an example of ultrasonic wave image corresponding to z-x plane illustrated in FIG. 8A.

FIG. 8 (which includes FIGS. 8A and 8B) are explanatory views illustrating principle of the welded state determination (secondary determination) performed by the stick weld determination element 59 of the determination unit 37, more specifically, FIG. 8A is a cross-sectional view (of z-x plane) of object to be inspected illustrating an example of real reflection (direct reflection and multiple reflection) occurring in the z-x plane, and FIG. 8B is an explanatory drawing illustrating an example of ultrasonic wave image corresponding to z-x plane illustrated in FIG. 8A. Here, for the sake of simplifying explanation, the object to be inspected 14 illustrated in FIG. 8 is plate-like structures 14a and 14b as an example of the object to be inspected 14.

Herein, as to the reference numerals illustrated in FIG. 8B, reference numeral 75 denotes line corresponding to the surface (upper plane) of the object to be inspected 14 illustrated in FIG. 8A, reference numeral 76 denotes line corresponding to the bottom of the plate-like structure 14a which is non-joined, of the object to be inspected 14 illustrated in FIG. 8A, reference numeral 77 denotes line corresponding to the bottom of the object to be inspected 14 illustrated in FIG. 8A, reference numeral 78 denotes presence region (which will be referred to as "direct reflection region", hereinafter) of the welded area 15 calculated on the basis of ultrasonic echo occurred by the direct reflection, reference numeral 79 denotes presence region (which will be referred to as "multiple reflection region", hereinafter) of the welded area 15 calculated on the basis of ultrasonic echo occurred by the multiple reflection, reference numeral 80 denotes region (which will be referred to as "temporarily acceptable region", hereinafter) which is present as meshes determined that the joined area 15 is sound (acceptable) in the open/small determination, reference numeral 82 denotes region (which will be referred to as "secondary determination region", hereinafter) which is present as meshes utilized in the secondary determination.

As illustrated in FIG. 8A, the reflected wave caused by the ultrasonic wave irradiated to the into the object to be inspected 14 includes the ultrasonic echo occurred by the multiple reflection such as the reflection waves R2, R4 and R5 as well as the ultrasonic echo occurred by the direct reflection, such as the reflection waves R1 and R3. In the secondary determination, the ultrasonic echo occurred by the multiple reflection such as the reflection waves R2, R4 and R5 illustrated as FIG. 8A is utilized.

In two-dimensional ultrasonic image illustrated in FIG. 8B, the length in z direction is proportional to the time elapsing from the time when the ultrasonic transducer 11 emits the ultrasonic wave to the object to be inspected 14 to the time when the ultrasonic wave emitted from the ultrasonic transducer 11. As a speed of the ultrasonic wave propagating through the object to be inspected 14 is considered as a constant, the length in z direction illustrated in FIG. 8B corresponds to a propagating distance (path length) of the ultrasonic wave. That is, the line 77 corresponding to the bottom of the object to be inspected 14 is emerged in central portion in right-and-left direction, of the object to be inspected 14 illustrated in FIG. 8A. The line 77 corresponding to the bottom of the object to be inspected 14 is based on reflection wave of the ultrasonic wave reflected at the bottom of the object to be inspected 14 and emerging every distance from the surface of the object to be inspected 14 to the bottom of the object to be inspected 14.

Thus, in the secondary determination performed by the stick weld determination element 59, the stick weld determination element 59 does not focus on the direct reflection region 78 but the stick weld determination element 59 focuses on the multiple reflection region 79. In FIG. 8A, the direct reflection region 78 is present between the line 75 denoting surface of object to be inspected 14 and the line 77, denoting bottom of object to be inspected 14, calculated on the basis of the reflection wave R3 directly reflected at the bottom of object to be inspected 14. In FIG. 8A, the multiple reflection region 79 is present between the line 77, denoting bottom of object to be inspected 14, calculated on the basis of the reflection wave R3 and the line 77 denoting bottom of object to be inspected 14, calculated on the basis of the reflection wave R5 twice reflected at the bottom of object to be inspected 14.

In the determination performed by the stick weld determination element 59, at first, the stick weld determination element 59 obtains information of position of mesh corresponding to the temporarily acceptable region 80 determined as "acceptance" in the primary determination from the open/small determination element 58. Subsequently, as illustrated in FIG. 8B, the stick weld determination element 59 extracts the region excluding predetermined region from the temporarily acceptable region 80 as the secondary determination region 82. For example, the secondary determination region 82 illustrated in FIG. 8B is obtained by excluding region which is located within predetermined distance from outer border of the temporarily acceptable region 80 from the temporarily acceptable region 80.

As an example, there is a case where the temporarily acceptable region 80 obtained by the stick weld determination element 59 is represented as a square corresponding to twenty-five (25) meshes arranged in a matrix being composed of five (5) meshes arranged in x direction and five (5) meshes arranged in y direction (5×5=25 meshes) and the predetermined distance is equal to the side length of one (1) mesh. In this case, the secondary determination region 82 corresponds to a residual region obtained by excluding meshes which is located within the side length of one (1) mesh from outer border of the temporarily acceptable region 80, the residual region which is located at central portion of the temporarily acceptable region 80 serving as a square having 5−2=3 meshes in each of x and y directions and therefore has 3×3=9 meshes arranged in a matrix.

After the secondary determination region 82 is determined, based on the intensity (reflection intensity) of the ultrasonic wave echo in z direction of each mesh on the x-y plane, obtained by the joint portion image creation unit 36, the stick weld determination element 59 compares the intensity of the ultrasonic wave echo at the depth position corresponding to the bottom of the first plate-like structure 14a in the multiple reflection region 79, i.e., the depth position (z coordinate) where the joined area 15 being in the stick weld state can be presented to the intensity of the ultrasonic wave echo at the same depth position of the normal object which includes the joined area 15 not being in the stick weld state. The intensity of the ultrasonic wave echo, obtained by inspecting the normal object (test piece) which has acceptable quality in another inspection method or the likes, as comparative criteria is preliminarily checked and thereafter readably stored in the stick weld determination element 59.

More detail, there is an example of determining the z coordinate set as the depth position corresponding to the bottom of the first plate-like structure 14*a* in the multiple reflection region 79. In this example, a depth position which is deviated from the position of the line 77 corresponding to the bottom of the object to be inspected 14 based on the reflection wave W3 at a distance in the depth direction is considered as the depth position where the joined area 15 being in the stick weld state can be presented. The distance in the depth direction corresponds to the thickness "ta" of the plate-like structure 14*a*. It is noted that z coordinate is determined on the basis of the plate combination information preliminarily stored in the plate combination information memorizing unit 56.

Here, in determination performed by the stick weld determination element 59, advantages of utilizing reflected wave caused by the multiple reflection instead of reflected wave caused by the direct reflection will be supplementarily described.

Figure 9A:
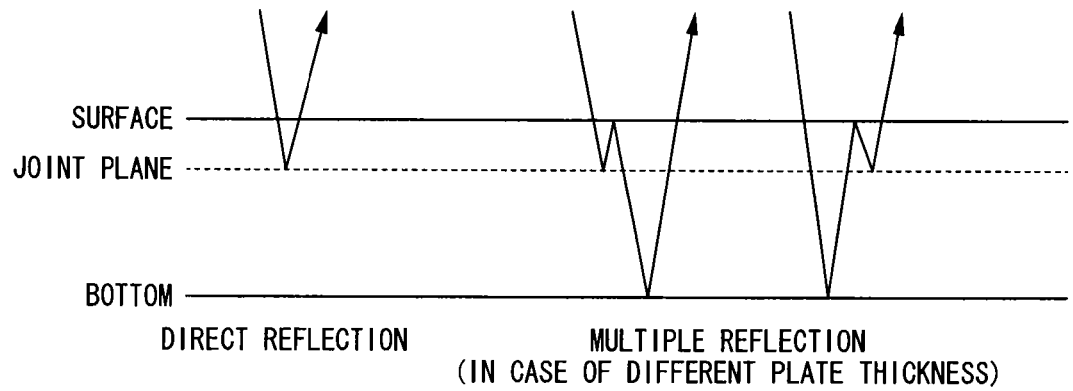
FIG. 9A is an explanatory drawing illustrating path of multiple reflection in a case where the thickness of each plate-like structure is different.
Figure 9B:
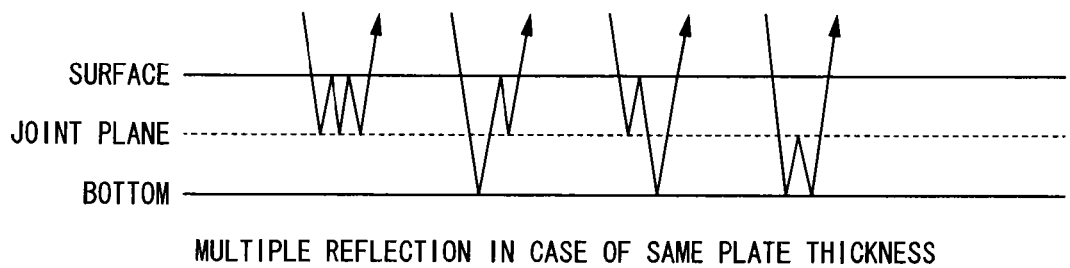
FIG. 9B is an explanatory drawing illustrating path of multiple reflection in a case where the thickness of each plate-like structure is same.

FIG. 9 (which includes FIGS. 9A and 9B) are explanatory views illustrating path of multiple reflection utilized in the welded state determination (the secondary determination) performed by the stick weld determination element 59. More specifically, FIG. 9A is an explanatory drawing illustrating path of multiple reflection in a case where the thickness of each plate-like structure is different and FIG. 9B is an explanatory drawing illustrating path of multiple reflection in a case where the thickness of each plate-like structure is same.

As illustrated FIG. 9A, in a case where the ultrasonic wave directly reflects at the joint plane (boundary layer) in the object to be inspected, the path of the ultrasonic wave which is same length is only one pathway (left side of FIG. 9A). Meanwhile, there is a case where the ultrasonic wave multiply reflects in the thickness of each plate-like structure as the object to be inspected. In above case, if each plate-like structure is same thickness, as illustrated FIG. 9A, the paths of the ultrasonic wave which is same length are two pathways (right side of FIG. 9A). Further, if each plate-like structure is not same (different) thickness, as illustrated FIG. 9B, the paths of the ultrasonic wave which is same length are four pathways. As described above, since the number of the path of the ultrasonic wave which is same length in multiple reflection case is larger than that in direct reflection case, useful information for the secondary determination is more increased. Therefore, if reflected wave caused by the multiple reflection is utilized, accuracy of the secondary determination in multiple reflection case can be more increased than accuracy of the secondary determination in direct reflection case.

If the distance that the ultrasonic wave propagates in some wave propagating medium is more increased or the number of the reflection of the ultrasonic wave is more increased, the ultrasonic wave would be more attenuated. Thus, in order that the z coordinate is properly selected, the attenuation of the ultrasonic wave should be considered. The multiple reflection region 79 can be extracted as the secondary determination region 82 is emerged between the line 77 corresponding to the bottom of the object to be inspected 14 calculated on the basis of the reflection wave p (herein, p is natural number which is more than 1) times reflected at the bottom of the object to be inspected 14 and the line 77 corresponding to the bottom of the object to be inspected 14 calculated on the basis of the reflection wave p+1 times reflected at the bottom of the object to be inspected 14. Since S/N (signal to Noise) tends to decrease with the increasing p as reflection number of times, it may not be preferable to extract the secondary determination region 82 from the multiple reflection region 79 in a case where reflection number of times is too many times such as in a case where the reflection number of times p is equal to 5 (p=5) or the likes.

Further, the determination unit 37 (the open/small determination element 58 and the stick weld determination element 59) is configured to be capable of setting the determination criteria utilized when the determination unit 37 determines whether the state of the joined area 15 is sound or not. The determination unit 37 sets at least one determination criteria selected from a plurality of determination criteria stored in the determination unit 37.

Examples of the determination criteria, determined by the open/small determination element 58, whether the state of the joined area 15 is sound or not are a diameter (or radius), an area or a thickness of the joined area 15, a result whether the indentation depth is shallower than predetermined depth, a result whether the area of the blowhole which is an example of the weld defect portion 28 is larger than predetermined area value (area rate) or the likes. Examples of the determination criteria, determined by the stick weld determination element 59, whether the state of the joined area 15 is sound or not are absolute intensity of the ultrasonic wave echo, relative intensity of the ultrasonic wave echo or the likes. Further, if the threshold values utilizing for the determination whether the state of the joined area 15 is sound or not are preset, the threshold values can be selected from all of the threshold values preset by the user.

The determination unit 37, configured in such a manner, determines whether the object to be determined satisfies the determination criteria or not by comparing the object to be determined with the determination criteria. If there is at least one object to be determined, the determination unit 37 can determine whether the object to be determined satisfies the determination criteria or not even with any combinations or any objects selected from at least one object to be determined. The determination unit 37 transmits the determination result whether the joined area 15 is sound or not to the display unit 38. After the determination unit 37 recognizes information updating operation by inputting the information updating operation to the determination unit 37, various information stored in the determination unit 37 can also be updated.

Next, the operation of the three-dimensional ultrasonic inspection apparatus 10 will be described.

In order to obtain the ultrasonic test image of the joined area 15, which is the inspection region (target region) of the object to be inspected, by means of the three-dimensional ultrasonic inspection apparatus 10, the ultrasonic transducer 11, which is a matrix sensor is activated.

The ultrasonic transducer 11 sequentially applies pulsed or continuous drive signals generated in the signal generating unit 12 to the matrix piezoelectric vibrators 20 one or plurality of pulses at a time and at a required timing, using the drive element selecting unit 13. When the piezoelectric vibrators 20 are selected by the drive element selecting unit 13 and the drive signals (electric signals) act to select the piezoelectric vibrators 20*mn*, the selected piezoelectric vibrators 20*mn* are subjected to piezoelectric transduction, and ultrasonic waves having required frequencies are produced.

The ultrasonic waves U produced by the piezoelectric vibrators 20*mn* enter the inspection region (joined area) 15 of the object to be inspected 14 through the acoustic wave propagating liquid medium 23 with a required spreading. The ultrasonic waves U entered the inspection region 15 of the object to be inspected 14 sequentially reach to boundary layers having different densities inside the object 14 and irradiated in a plane. A portion of the ultrasonic waves plane (two-dimensional)-irradiated inside the object 14 is reflected at the boundary layer, and the reflected wave enters the matrix sensor 11 through the acoustic wave propagating liquid medium 23 as a reflected echo and enters the piezoelectric vibrators 20.

Each piezoelectric vibrators 20 in which the reflected echo entered, acts as piezoelectric transducing elements, and transmits an electric signal depending on the magnitude of the reflected echo to the signal detecting circuit 16. Since a large number of piezoelectric vibrators 20$mn$ are provided to the ultrasonic transducer 11 constituting the matrix sensor 11, the ultrasonic waves sequentially produced by the piezoelectric vibrators 20$mn$ with different oscillation positions, sequentially reflected at the joined area (inspection region) of the object 14, enter the matrix sensor 11 as reflected echoes, and are sequentially transmitted from the piezoelectric vibrators 20 of the matrix sensor 11 to the signal detecting circuit 16 as electric signals of the reflected echoes.

Thereafter, the electric signals of the reflected echoes transmitted to the signal detecting circuit 16 enter the signal processing unit 17, the electric signals of the reflected echoes are subjected to signal processing in the signal processing unit 17, and the three-dimensional imaging data is made by the parallel processor 33 of the joined area 15, which is the inspection region of the object to be inspected and the three-dimensional image generating unit 34.

At that time, since the signal processing unit 17 is equipped with the parallel processor 33, and the electric signals of the reflected echoes input to the signal processing unit 17 are subjected to an arithmetic processing in parallel by the parallel processor 33, the rapid arithmetic processing can be performed in a short time.

The three-dimensional image generating unit 34 generates three plane images by seeing through the three-dimensional imaging data from three directions, which are a front direction viewed from the ultrasonic transducer 11 and two directions perpendicular to the front direction and each other and by projecting the largest value data of the imaging data superposing in the see-through directions of the three-dimensional imaging data in each three directions on a plane.

Since the imaging data of the sides perpendicular to the front includes a large number of information in the thickness direction of the plurality of plate-like objects to be inspected 14 having the joined area 15, and the reflection intensity from the bottom of the first plate-like structure 14$a$ viewed from the transducer 11 is high in the non-joined area in which the plate-like objects are not joined together, the bottom position of the plate-like structure 14$a$ can be determined. Meanwhile, since, in the area where the plurality of plate-like objects 14 are joined together, the transmittance of the ultrasonic wave is high, the position of the bottom portion 29 of the plurality of plate-like objects 14 can be determined as the area having the highest reflection intensity.

The joint portion data processing unit 35 can detect the first and second peaks of the intensity distribution in depth direction (z axis direction) at each position (x, y) based on the three-dimensional imaging data I, and then transmits detection result to the joint portion image creation unit 36. The joint portion image creation unit 36 calculates each depth at which the ultrasonic wave reflects at each position (x, y) by calculating the distance between the depth position at which the first peak appears and the depth position at which the second peak appears and then creates the three-dimensional image of the joined area 15. If the user has only to view (checks) the three-dimensional image of the joined area 15 (the joined area image), the user can immediately recognize shape information such as the profile shape, the size, the position or the likes of the joined area 15 and the position of the weld defect portion 28. The joint portion image creation unit 36 transmits the three-dimensional image of the joined area 15 generated by the joint portion image creation unit 36 and the result measured by the joint portion image creation unit 36 to the determination unit 37 and the display unit 38.

The determination unit 37 receives the three-dimensional image of the joined area 15 generated by the joint portion image creation unit 36 and the measurement result. The open/small element 58 performs the open/small determination (preliminary determination). In the open/small determination, the object to be inspected 14 being in the open/small state and/or the small state is excluded. Subsequently, with respect to the object to be inspected 14 not being in the open/small state and the small state, i.e., the object to be inspected 14 which passes in the open/small determination, the stick weld determination element 59 performs the stick weld determination (secondary determination).

The determination unit 37 transmits information including at least one of the three-dimensional image of the joined area 15 created by the joint portion image creation unit 36, measurement result, open/small determination result and stick weld determination result to the display unit 38. The information transmitted from the determination unit 37 is displayed on the display unit 38.

According to the three-dimensional ultrasonic wave inspection apparatus 10, configured in such a manner, as the accuracy of the inner inspection using ultrasonic waves can be increased (improved), automatic determination of inspection can be achieved. Further, the three-dimensional ultrasonic wave inspection apparatus 10 can provide the image enabled the user immediately to recognize the state of the joined area 15 whether the joined area 15 is sound or not, the range of the weld defect portion 28 and so on to users. Furthermore, even if the known the three-dimensional ultrasonic wave inspection apparatus can not accurately determine the state of the joined area 15 cause of the joined area image created by obliquely slicing the object to be inspected 14, the three-dimensional ultrasonic wave inspection apparatus 10 can prevent from creating the joined area image in a state where the object to be inspected 14 is obliquely slicing cause of performing the attenuation correction processing. Therefore, according to the three-dimensional ultrasonic wave inspection apparatus 10, the state of the joined area 15 can be accurately determined.

In addition, the three-dimensional ultrasonic wave inspection apparatus according to the present invention is not limited to that described in the above-mentioned embodiment, other various kinds of modifications may be considered.

One embodiment of the three-dimensional ultrasonic wave inspection apparatus adopts a configuration in which the signal processing unit 17 and display processing device 18 are included in the three-dimensional ultrasonic wave inspection apparatus 10 was used. However, the three-dimensional ultrasonic wave inspection apparatus can be provided by using independent computers. Further, the three-dimensional image generating unit 34 of the signal processing unit 17 may be included by shifting it into the display processing device 18.

The computers have functions of performing each processing in the present embodiment, and may have any configuration such as a computer apparatus composed of one device such as a personal computer, or a computer system where a plurality of computer apparatuses are connected in a network. Further, as for the computer, it is not limited to the personal computer, an arithmetic processing device included in communication devices and information processing devices, and a microcomputer may be included, and it is a generic term of devices and apparatuses enabling to perform the function of the present invention by means of program.

Furthermore, the internal configuration of the display processing device 18 can be provided by using a software. The software may be a memory in a computer readable memory medium such as a flexible disk, and may be a type that is transferred on a network such as a LAN or an internet as a software (program) single body. In this case, by reading out the software (program) memorized in the memory medium and by downloading the software (program) from a site (server) on the LAN or the internet to install a hard disk, it is possible to perform processing in the computer.

In other words, as for the software (program) in the present invention, it is not limited to those which memorized in a memory medium independent to the computer, and a type distributed through a transmitting medium such as the LAN or the internet may be included.

In addition, as for the program, if it is memorized in a memory medium such as a memory, a flexible disk, a hard disk, an optical disk (CD-ROM, CD-R, DVD etc.), a magneto-optical disk (MO etc.), and a semiconductor memory in a computer readable manner, its language format and memory format may be taken freely.

Moreover, based on the instruction of a program installed in the computer, a portion of each processing for achieving the present embodiment may be performed by an MW (middleware) etc. such as an OS (operating system), a database-management software, a network software.

Further, as for the memory medium, it is not limited to media independent to the computer, and memory media where a program transmitted by the LAN or the internet etc. is downloaded and memorized or temporarily memorized, may be included. Moreover, the memory medium is not limited to one, and, when the procedures in the present embodiment are performed using a plurality of media, the media may be also included in the memory media in the present embodiment, and the configuration of the media may be taken by any configuration.

REFERENCE NUMERALS

10 . . . three-dimensional ultrasonic inspection apparatus, 11 . . . ultrasonic transducer (matrix sensor), 12 . . . signal generating unit, 13 . . . driving element selecting unit, 14 . . . object to be inspected, 14a, 14b, 14c . . . plate-like structure (object to be inspected), 15 . . . joined portion (welded area, inspection region, target region), 16 . . . signal detecting circuit, 17 . . . signal processing unit, 18 . . . display processing device, 20 (20mn) . . . piezoelectric vibrators, 21 . . . board, 23 . . . acoustic wave propagating medium, 24 . . . couplant, 25 . . . concave portion (dent portion), 26 . . . non-joined area, 27 . . . molten-solidified portion, 28 . . . weld defect portion, 29 . . . bottom, 31a, 31b, . . . , and 31i . . . amplifier, 32a, 32b, . . . , and 32i . . . A/D converter, 33 . . . parallel processors, 34 . . . three-dimensional image generating unit (image synthesis processor), 35 . . . joint portion data processing unit, 36 . . . joint portion image creation unit, 37 . . . determination unit, 38 . . . display unit, 40a, 40b, . . . , and 40i . . . inner memory, 41a, 41b, . . . , and 41i . . . processing (arithmetic) circuits, 44 . . . image synthesis processing unit, 45 . . . boundary extraction processing unit, 46 . . . shape data memorizing unit, 47 . . . table data storing unit, 51 . . . first peak detecting element, 52 . . . second peak detecting element, 53 . . . attenuation correction processing element (first correction processing element), 54 . . . inverse correction processing element (second correction processing element), 56 . . . plate combination information memorizing unit, 58 . . . open/small determination element, 59 . . . stick weld determination element, 61 . . . first peak, 62 . . . second peak, 71 . . . first peak detecting element, 75 . . . line denoting surface of object to be inspected, 76 . . . line denoting bottom of plate-like structures which are not joined, 77 . . . line denoting bottom of object to be inspected, 78 . . . direct reflection region, 79 . . . multiple reflection region, 80 . . . temporarily acceptable region, 82 . . . stick weld determination region, ta, tb and tc . . . thickness of the plate-like structures, m1, m2, m3 . . . mesh, R1, R2, R3, R4, R5 . . . reflection wave.

The invention claimed is:

1. A three-dimensional ultrasonic inspection apparatus comprising:

an ultrasonic transducer in which a plurality of piezoelectric vibrators are disposed in a matrix or an array;

a driving element selecting unit to sequentially select piezoelectric vibrators from the plurality of piezoelectric vibrators disposed in the ultrasonic transducer to produce an ultrasonic wave;

a signal detecting circuit to cause the ultrasonic wave generated by the piezoelectric vibrator selected by the drive element selecting unit to propagate through an acoustic wave propagating medium and enter a joined area of an object to be inspected for receiving a reflected echo from the joined area, and to detect an electric signal corresponding to the reflected echo from the joined area;

a signal processing unit to subject the electric signal detected by the signal detecting circuit to signal processing, and to generate three-dimensional imaging data by causing the electric signal to correspond to a mesh element partitioned in a three-dimensional imaging region set inside the object to be inspected;

a first peak detecting unit to detect a first peak of the intensity distribution of the three-dimensional imaging data in depth direction (z direction), the first peak primarily appearing at a depth position being deeper than a reference depth;

a second peak detecting unit to detect a second peak of the intensity distribution of the three-dimensional imaging data in depth direction, the second peak primarily appearing at a depth position being deeper than the depth position at which the first peak appears;

a joint portion image creation unit to create a three-dimensional image of a joined area by mapping a distance, between the depth position at which the first peak appears and the depth position at which the second peak appears, in depth direction at each position on x-y plane;

an open/small determination unit to determine whether a blowhole in the joined area is absent and a size of molten-solidified portion of the joined area satisfies a determination criteria in accordance with the three-dimensional image of the joined area created by the joint portion image creation unit and the determination criteria which is preset;

a stick weld determination unit to determine whether the joined area determined whether the blowhole in the joined area is absent and the size of molten-solidified portion of the joined area satisfies the determination criteria is tightly joined each other without melting; and a display unit to display at least one of the three-dimensional image and at least one of a result determined by the open/small determination unit and a result determined by the stick weld determination unit.

2. The three-dimensional ultrasonic inspection apparatus according to claim 1, wherein the image generating unit measures a size and a position of the joined area and a welded defect, existed in the object to be inspected by detecting the size and the position of the joined area and the welded defect based on the three-dimensional image of the joined area, and transmits a result of measuring the size and the position of the joined area and the welded defect to the determination unit and the display unit.

3. The three-dimensional ultrasonic inspection apparatus according to claim 1, wherein the image generating unit to identify a size and a position of a closing region, in a continuum region, as a welded defect when the image generating unit determines that the closing region existing at one depth zone exists in the continuum region existing another depth zone on the x-y plane based on the three-dimensional image of the joined area.

4. The three-dimensional ultrasonic inspection apparatus according to claim 1, further comprising a plate combination information memorizing unit to store a plate combination information including thickness information of each plate which constitutes a plate combination as the object to be inspected, wherein the joint portion image creation unit configured to calculate a depth position, from the surface of the object to be inspected, obtained by calculating a distance, between the depth position at which the first peak appears and the depth position at which the second peak appears, in depth direction at each position on x-y plane, and plot the depth position at each position on x-y plane by determining that the depth position is place at any one of each combined position obtained by referring the plate combination information stored in the plate combination information memorizing unit in accordance with a relation between the depth position and each combined position obtained by referring the plate combination information stored in the plate combination information memorizing unit.

5. The three-dimensional ultrasonic inspection apparatus according to claim 1, further comprising a first correction processing unit to perform a correction processing so as to increase an intensity of the reflection echo in depth direction of the three-dimensional image data of the object to be inspected as a depth increases.

6. The three-dimensional ultrasonic inspection apparatus according to claim 1, further comprising a second correction processing unit to perform a correction processing so as to be forced to attenuate an intensity of the reflection echo in depth direction of the three-dimensional image data of the object to be inspected as a depth increases.

7. The three-dimensional ultrasonic inspection apparatus according to claim 1, wherein the stick weld determination unit determinates whether the joined area determined whether the blowhole in the joined area is absent and the size of molten-solidified portion of the joined area satisfies the determination criteria is tightly joined each other without melting based on difference between a reflection intensity of an ultrasonic wave echo obtained from an object to be inspected which is acceptable quality and a reflection intensity of an ultrasonic wave echo obtained from an object to be inspected in which stick weld portion is exist.

8. The three-dimensional ultrasonic inspection apparatus according to claim 1, wherein the joined area determined whether the blowhole in the joined area is absent and the size of molten-solidified portion of the joined area satisfies the determination criteria is tightly joined each other without melting based on an intensity of a multiply-reflected ultrasonic wave echo.

* * * * *